US010512673B2

(12) United States Patent
Tarasova et al.

(10) Patent No.: US 10,512,673 B2
(45) Date of Patent: Dec. 24, 2019

(54) USE OF PEPTIDE-BASED INHIBITORS OF THE STAT3-IL10 PATHWAY FOR TREATING BACTERIAL INFECTION AND GRANULOMATOUS DISEASE

(71) Applicants: The United States of America, as Represented by the Secretary, Department of Health and Human Services, Bethesda, MD (US); Colorado State University Research Foundation, Fort Collins, CO (US)

(72) Inventors: Nadya I. Tarasova, Frederick, MD (US); Mercedes Gonzalez-Juarrero, Fort Collins, CO (US)

(73) Assignees: The United States of America, as represented by the Secretary, Department of Health and Human Services, Bethesda, MD (US); Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 15/541,871

(22) PCT Filed: Jan. 7, 2016

(86) PCT No.: PCT/US2016/012493
§ 371 (c)(1),
(2) Date: Jul. 6, 2017

(87) PCT Pub. No.: WO2016/112193
PCT Pub. Date: Jul. 14, 2016

(65) Prior Publication Data
US 2018/0000901 A1 Jan. 4, 2018

Related U.S. Application Data

(60) Provisional application No. 62/100,763, filed on Jan. 7, 2015.

(51) Int. Cl.
| | | |
|---|---|---|
| A61K 38/20 | (2006.01) | |
| A61K 45/06 | (2006.01) | |
| A61K 38/17 | (2006.01) | |
| A61K 9/00 | (2006.01) | |
| A61K 9/12 | (2006.01) | |
| C07K 7/06 | (2006.01) | |
| C07K 7/08 | (2006.01) | |

(52) U.S. Cl.
CPC .......... *A61K 38/2066* (2013.01); *A61K 9/007* (2013.01); *A61K 9/12* (2013.01); *A61K 38/1709* (2013.01); *A61K 38/1793* (2013.01); *A61K 45/06* (2013.01); *C07K 7/06* (2013.01); *C07K 7/08* (2013.01)

(58) Field of Classification Search
CPC ............ A61K 38/1709; A61K 38/1793; A61K 38/2066; A61K 45/06; A61K 9/007; A61K 9/12
See application file for complete search history.

(56) References Cited

U.S. PATENT DOCUMENTS

| | | | |
|---|---|---|---|
| 2010/0168015 A1* | 7/2010 | Manterola Careaga | ..................... C07K 14/5428 514/13.3 |
| 2010/0184697 A1* | 7/2010 | Tarasova | ............ C07K 14/4705 514/21.2 |

FOREIGN PATENT DOCUMENTS

| | | |
|---|---|---|
| WO | WO 2000/063241 A2 | 10/2000 |
| WO | WO 2008/151037 A1 | 12/2008 |
| WO | WO 2011/143280 A2 | 11/2011 |

OTHER PUBLICATIONS

Carole D. Mitnick, Tuberculosis pharmacotherapy: strategies to optimize patient care, Expert Opin Pharmacother. Feb. 2009 ; 10(3):381-401.*
Cheng-Rong Yu, Therapeutic Targeting of STAT3 (Signal Transducers and Activators of Transcription 3) Pathway Inhibits Experimental Autoimmune Uveitis, PLoS One 7(1): e29742S, 2012.*
Murray Goodman, On the Concept of Linear Modified Retro-Peptide Structures, Accounts of chemical research, vol. 12, No. 1, Jan. 1979.*
T. Holm, Cell-penetrating peptides as antifungals towards Malassezia sympodialis, Letters in Applied Microbiology ISSN 0266-8254, 2011, 54, pp. 39-44.*
Cyktor JC et al. IL-10 Inhibits Mature Fibrotic Granuloma Formation during *Mycobacterium tuberculosis* Infection. Journal of Immunology, vol. 190, No. 6, Mar. 15, 2013, pp. 2778-2790.
International Search Report and Written Opinion, PCT/US2016/012493, dated May 18, 2016.
O'Kane CM et al. STAT3, p38 MAPK, and NF-kappaB Drive Unopposed Monocyte-Dependent Fibroblast MMP-1 Secretion in Tuberculosis. American Journal of Respiratory Cell and Molecular Biology, vol. 43, No. 4, Oct. 2010, pp. 465-474.

(Continued)

*Primary Examiner* — Rachael E Bredefeld
*Assistant Examiner* — Erinne R Dabkowski
(74) *Attorney, Agent, or Firm* — Polsinelli PC

(57) ABSTRACT

The invention provides a method of treating pathogenic bacterial infection (e.g., tuberculosis infection) in an animal comprising administering a peptide-based inhibitor of the STAT3-IL10 pathway or a nucleic acid encoding the peptide-based inhibitor to the animal. The invention also provides methods of treating chronic granulomatous disease and Wegener's granulomatosis in an animal comprising administering a peptide-based inhibitor of the STAT3-IL10 pathway or a nucleic acid encoding the peptide-based inhibitor to the animal.

20 Claims, 10 Drawing Sheets
Specification includes a Sequence Listing.

(56) References Cited

OTHER PUBLICATIONS

Rottenberg ME et al. SOCS3 and STAT3, major controllers of the outcome of infection with *Mycobacterium tuberculosis*. Seminars in Immunology, vol. 26, No. 6, Dec. 1, 2014, pp. 518-532.
Wieczorek S et al. Functionally Relevant Variations of the Interleukin-10 Gene Associated with Antineutrophil Cytoplasmic Antibody-Negative Churg-Strauss Syndrome, but not with Wegener's Granulomatosis. Arthritis & Rheumatism, vol. 58, No. 6, Jun. 2008, pp. 1839-1848.
Timofeeva OA et al. Rationally Designed Inhibitors Identify STAT3 N-Domain as a Promising Anticancer Drug Target. ACS Chemical Biology. Dec. 21, 2007;vol. 2 No. 12:799-809.

\* cited by examiner

USE OF PEPTIDE-BASED INHIBITORS OF THE STAT3-IL10 PATHWAY FOR TREATING BACTERIAL INFECTION AND GRANULOMATOUS DISEASE

CROSS-REFERENCE TO RELATED APPLICATIONS

This patent application claims the benefit of U.S. Provisional Patent Application No. 62/100,763, filed Jan. 7, 2015, which is incorporated by reference.

GOVERNMENT SUPPORT

This invention was made with government support under Grants AI105585 and AI102210 awarded by the National Institutes of Health. The government has certain rights in the invention.

SEQUENCE LISTING

Incorporated by reference in its entirety herein is a computer-readable nucleotide/amino acid sequence listing submitted concurrently herewith.

BACKGROUND OF THE INVENTION

Current chemotherapy for tuberculosis (TB) fails to eliminate rapidly the *Mycobacterium tuberculosis* (Mtb) bacilli and to control TB globally. Treatment for drug-susceptible TB today requires 6-9 months of multidrug therapy (see Whorwell, World Health Organization (WHO). Global tuberculosis report 2013. http://apps.who.int/iris/bitstream/10665/91355/1/9789241564656_eng.pdf (2013)). As for TB patients with multi drug resistant (MDR)-TB infections, treatment is endured for two years and is unsuccessful in more than 50% of the cases.

To improve TB control globally, shorter, effective, and well-tolerated treatments for latent TB infection is desired as this is the only way to reduce the development of resistance against the new chemical entities.

BRIEF SUMMARY OF THE INVENTION

The invention provides a method of treating a pathogenic bacterial infection in an animal comprising administering a peptide-based inhibitor of the STAT3-IL10 pathway or a nucleic acid encoding the peptide-based inhibitor to the animal, thereby treating the pathogenic bacterial infection in the animal.

The invention provides a method of treating chronic granulomatous disease in an animal comprising administering a peptide-based inhibitor of the STAT3-IL10 pathway or a nucleic acid encoding the peptide-based inhibitor to the animal, thereby treating chronic granulomatous disease in the animal.

The invention also provides a method of treating Wegener's granulomatosis in an animal comprising administering a peptide-based inhibitor of the STAT3-IL10 pathway or a nucleic acid encoding the peptide-based inhibitor to the animal, thereby treating Wegener's granulomatosis in the animal.

BRIEF DESCRIPTION OF THE SEVERAL VIEWS OF THE DRAWINGS

In FIG. 2A, the $Log_{10}$ of colony forming units (CFU) obtained from lung samples of each mouse in the group of mice not receiving treatment (n=5) or mice treated with the peptide inhibitors IL10R1-7 (n=5), IL10R1-14 (n=4), and ST3-H2A2 (n=5) are shown. Data represent mean±SD of 5 mice per group and means±SD of triplicates where * denote $p<0.05$;  denotes $p<0.01$; and * denotes $p<0.001$ by Student's t test. In FIG. 2B, mice were weighed at the beginning (grey bars) and end (black bars) of therapy.

In FIGS. 3A and 3B, lung samples from mice were analyzed by RT-PCR for mRNA transcript expression of stat 3 and Il-10 using lung homogenates of C57BL/6 mice based on the expression of 18S. The lungs were harvested and samples were collected in Trizol for RNA extraction and RT-PCR assay. Samples were homogenized and RT-PCR analysis was performed to detect and quantify stat3 (A) or Il-10 (B) mRNA. In FIGS. 3C and 3D, lung homogenates were assayed by ELISA for pSTAT3 (C) or by CBA for IL-10 cytokine (D). Peptide inhibitor treatment regimens are indicated as: No treatment (white bars), IL10R1-7 treatment (grey bars), IL10R1-14 (striped bars) and ST3-H2A2 (black bars). Data represent mean±SD of 5 mice per group and means±SD of triplicates where * denotes $p<0.05$;  denotes $p<0.01$; and * denotes $p<0.001$ by Student's t test.

In FIGS. 4A and 4B, RNA samples were assayed by real-time RT-PCR to determine expression of nos2 (A) and arg-1 (B). In FIGS. 4C-4F, lung homogenates from each mouse were used to determine the activity of the NOS-2 nitrite and nitrate (C) by the Griess reaction. Arginase (D), lysozyme (F), and NADPH (E) activities also were measured. Data represent mean±SD of n=5 and means±SD of triplicates where * denotes $p<0.05$;  denotes $p<0.01$; and * denotes $p<0.001$ by Student's t test.

In FIGS. 6A-6D, lung samples from mice were analyzed by RT-PCR for mRNA transcript expression of bcl-2 (A), bax-2 (C), atg-5 (B), and beclin-1 (D) using lung homogenates of C57BL/6 mice based on the expression of 18S. The lungs were harvested and samples were collected in Trizol for RNA extraction and RT-PCR assay. In FIGS. 6E and 6F, lung homogenates were assayed by ELISA for Bcl-2 (E) and Atg-5 (F). Data represent mean±SD of 5 mice per group and means±SD of triplicates where *, denotes p<0.05;  denotes p<0.01; and * denotes p<0.001 by Student's t test.

DETAILED DESCRIPTION OF THE INVENTION

Figure 1A:
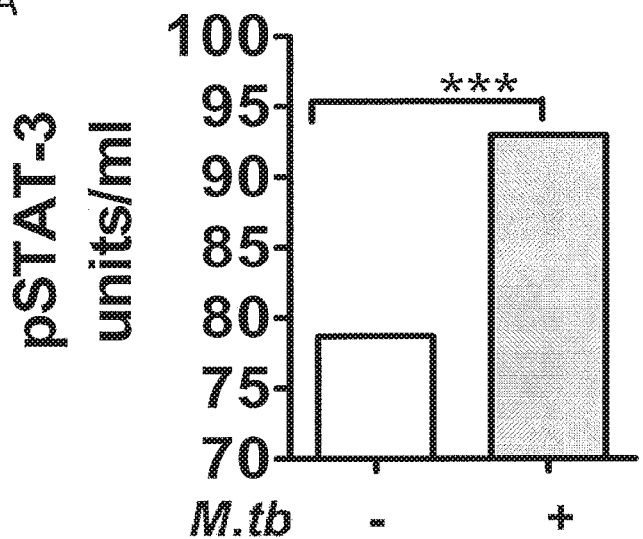
FIGS. 1A and 1B are tables illustrating the elevated expression of pSTAT-3 (A) and IL-10 (B) in the lungs of mice chronically infected with Mtb. Lung homogenates obtained from naïve (white bars) or chronically Mtb (shaded bars) C57BL/6 mice (n+5) were assayed by ELISA for pSTAT3 (A) or by cytometric bead assay (CBA) for IL-10 (B) to compare the levels of expression between groups of mice.

The invention is predicated on the discovery that peptide inhibitors of the STAT3-IL10 pathway significantly reduced bacterial load in mice infected with *Mycobacterium tuberculosis* (Mtb) bacilli even in the absence of antibiotics. Moreover, exposure to the peptide inhibitors modulated the lung host immune response to enhance its own bactericidal capacity.

Therefore, the invention provides a method of stimulating an immune response in an animal comprising administering a peptide-based inhibitor of the STAT3-IL10 pathway or a nucleic acid encoding the peptide-based inhibitor to the animal, thereby stimulating an immune response in the animal. In one embodiment, the immune response is stimulated against an infectious disease.

The invention provides a method of treating a pathogenic bacterial infection in an animal comprising administering a peptide-based inhibitor of the STAT3-IL10 pathway or a nucleic acid encoding the peptide-based inhibitor to the animal, thereby treating the pathogenic bacterial infection in the animal. In one embodiment, the pathogenic bacterial infection is tuberculosis. In another embodiment, the pathogenic bacterial infection is an infection of a bacterium of the family Mycobacteriaceae, such as an infection of *Mycobacterium tuberculosis*. The treatment method preferably results in reduced *Mycobacterium tuberculosis* (Mtb) bacilli load in the lungs of the animal.

Tuberculosis is associated with granulomas in the lung. In addition to tuberculosis, the invention provides methods of treating two other conditions that are associated with granulomas in the lung: chronic granulomatous disease and granulomatosis with polyangiitis (Wegener's granulomatosis). In particular, the invention provides a method of treating chronic granulomatous disease comprising administering a peptide-based inhibitor of the STAT3-IL10 pathway or a nucleic acid encoding the peptide-based inhibitor to the animal, thereby treating chronic granulomatous disease in the animal. The invention also provides a method of treating Wegener's granulomatosis comprising administering a peptide-based inhibitor of the STAT3-IL10 pathway or a nucleic acid encoding the peptide-based inhibitor to the animal, thereby treating Wegener's granulomatosis in the animal.

The animal to be treated can be any suitable animal including, but not limited to, mice, rats, guinea pigs, hamsters, rabbits, cats, dogs, pigs, sheep, cows, horses, and primates, such as monkeys, apes, or humans. In one embodiment, the animal is a human patient.

The peptide-based inhibitor can be any suitable inhibitor including peptides and peptidomimetics. Preferably, the peptide-based inhibitor is a peptide or peptidomimetic of STAT3 (preferably, STAT3 N-terminal domain) or interleukin 10 (IL-10). Exemplary peptides and peptidomimetics are described in U.S. Patent Application Publication Nos. 2010/0184697 and 2013/0109619, Timofeeva et al. (*ACS Chem. Biol.*, 2(12): 799-809 (2007)), Timofeeva et al. (*Proc. Natl. Acad. Sci. USA*, 110(4): 1267-72 (2013)), and described herein. Preferably, the peptide-based inhibitor is a non-naturally occurring peptide or peptidomimetic.

Without wishing to be bound by any particular theory or mechanism of action, it is believed that IL10 signals through a heterodimeric receptor, and the peptides and peptidomimetic compounds interfere with the formation of the signaling complexes. The extracellular domain of the recombinant human IL10 receptor, when bound to IL10 forms a complex containing two IL10 homodimers and four receptor monomers. In addition, a single IL10 dimer could bind two receptors. IL10 binding leads to the phosphorylation and activation of STAT3 transcription factor. It is believed that the peptides and peptidomimetics can act as dominant negative inhibitors of the cytoplasmic domains, or as inhibitors of the cytokine dimerization and assembly.

The sequences of IL10, IL10R1, and IL10R2 are known in the art, and available in publicly accessible databases, for example, UniGene Accession Nos. Hs.193717, Hs.504035, and Hs.654593. The family of STAT proteins also is well known in the art. In particular, STAT3 is provided by UniGene Accession Hs.463059.

According to one aspect of the invention, the peptide or peptidomimetic comprises the sequence $x^1VLx^4Fx^6K$ (SEQ ID NO: 1), wherein x can be any amino acid. Desirably, $x^1$ is $\underline{S}$, T, or A; $x^4$ is V or $\underline{L}$; and $x^6$ is E or K, wherein more preferred residues are underlined. For example, the peptide or peptidomimetic can comprise the sequence SVLLFKK (SEQ ID NO: 2). Other examples of such sequences comprise any of SEQ ID NOs: 3-7.

In another aspect of the invention, the peptide or peptidomimetic comprises the sequence $LHGSTx^6SGFGSx^{12}K$ (SEQ ID NO: 21) or $LHGSTx^6SGFGSx^{12}KPSLQx^{18}$ (SEQ ID NO: 8), wherein x can be any amino acid. Desirably, $x^6$ is D or N, $x^{12}$ is $\underline{T}$, A, or G, and $x^{18}$ (if present) is $\underline{T}$ or N, with preferred residues underlined. By way of further illustration, such a peptide can comprise the sequence LHGSTx-SGFGSTKPSLQT (SEQ ID NO: 9), wherein $x^6$ is D or N. More specific examples of such peptides comprise any of SEQ ID NOs: 10-16 and 35.

According to another aspect of the invention, the peptide or peptidomimetic comprises the sequence TDSGICLQ (SEQ ID NO: 17). By way of further illustration, such a peptide or peptidomimetic can comprise any of SEQ ID NOs: 18 or 19.

According to another aspect of the invention, the peptide or peptidomimetic comprises the sequence $Fx^2GYx^5x^6QTR$ (SEQ ID NO: 20), wherein x can be any amino acid. Desireably, $x^2$ is Q or R; $x^5$ is L or Q; and $x^6$ is R or K, wherein more preferred residues are underlined. By way of further example, such a peptide can comprise any of SEQ ID NOs: 22-24.

According to another aspect of the invention, the peptide or peptidomimetic comprises the sequence AxGYLKQ (SEQ ID NO: 25), wherein x can be any amino acid. Desirably, x is K, A, or T, preferably K. By way of further illustration, such a peptide can comprise any of SEQ ID NOs: 26-29.

According to another aspect of the invention, the peptide or peptidomimetic comprises the sequence LVTLPLISSL (SEQ ID NO: 30). By way of further illustration, such a peptide can comprise any of SEQ ID NOs: 31-34.

According to another aspect of the invention, the peptide or peptidomimetic comprises the sequence $Px^2HLKEx^7L$ (SEQ ID NO: 36), wherein x can be any amino acid. Desirably, $x^2$ is E or Q, and $x^7$ is Y or F.

TABLE 1

| Compound | Sequence | SEQ ID |
|---|---|---|
| IL10R1-1 | Pal-LYVRRRKKL<u>PSVLLFKK</u>-NH$_2$ | 3 |
| IL10R1-3 | ε-Pal-KKL<u>PSVLLFKK</u>PS-NH$_2$ | 4 |
| IL10R1-9 | Ac-SP<u>KKFLLVS</u>PLKK-ε-Pal (All-D) | 5 |
| IL10R1-10 | Ac-<u>KKFLLVS</u>PLKK-ε-Pal (All-D) | 6 |
| IL10R1-11 | Ac-<u>PKKFLLVS</u>PLKK-ε-Pal (All-D) | 7 |

*The regions believed to be involved in interactions with JAK1 are underlined.

TABLE 2

*IL10R1-23 and IL10R1-2 are cyclic peptides with a disulfide bond bridging the two cysteine residues.

| | Compound | Sequence | SEQ ID |
|---|---|---|---|
| Conserved region B | IL10R1-4 | Pal-LHGSTDSGFGSTK | 35 |
| | IL10R1-5 | Pal-LHGSTDSGFGSTKPSLQT | 10 |
| | IL10R1-14 | Ac-EETQLSPKTSGFGSDTSGHLK-E-Pal (All-D) | 11 |
| | IL10R1-15 | Ac-ETQLSPKTSGFGSDTSGHLK-s-Pal (All-D) | 12 |
| | IL10R1-16 | Ac-TQLSPKTSGFGSDTSGHLK-e-Pal (All-D) | 13 |
| | IL10R1-17 | ε-Pal-KTQLSPKTSGFGSDTSGHL-NH$_2$ (All-D) | 14 |
| | IL10R1-18 | ε-Pal-KEETQLSPKTSGFGSDTSGHL-NH$_2$ (All-D) | 15 |
| | IL10R1-25 | ε-Pal-KTQLSPKTSGFGSNTSGHL-NH$_2$ (All-D) | 16 |
| Conserved region C | IL10R1-23 | ε-Pal-KTCGDNTDSGICLQ-NH$_2$ (cyclic)* | 18 |
| | IL10R1-2 | ε-Pal-KSCSSGSSNSTDSGICLQ (cyclic)* | 19 |
| Region D, STAT3-binding | IL10R1-22 | ε-Pal-KFQGYLRQTR-NH$_2$ | 22 |
| | IL10R1-24 | Pal-AFQGYLRQTR-NH$_2$ | 23 |
| | IL10R1-26 | Ac-RTQRLYGQFK-ε-Pal (All-D) | 24 |
| Region E, STAT3-binding | IL10R1-8 | ε-Pal-KPPALAKGYLKQ-NH$_2$ | 26 |
| | IL10R1-19 | ε-Pal-KPPALAKGYLKQE-NH$_2$ | 27 |
| | IL10R1-20 | ε-Pal-KAKGYLKQ-NH$_2$ | 28 |
| | IL10R1-21 | Pal-LAKGYLKQ-NH$_2$ | 29 |
| Conserved Region F | IL10R1-7 | ε-Pal-KLVTLPLISSLQSSE-NH$_2$ | 31 |
| | IL10R1-27 | ε-Pal-KLVTLPLISSLQ-NH$_2$ | 32 |
| | IL10R1-28 | ε-Pal-KLVTLPLISSL-NH$_2$ | 33 |
| | IL10R1-29 | ε-Pal-KNLVTLPLISSL-NH$_2$ | 34 |

According to another aspect of the invention, the peptide or peptidomimetic comprises the sequence SEFDI-FINYIEAY (SEQ ID NO: 37), optionally as a dimeric compound. For instance, the dimeric compound can comprise two regions, each comprising the sequence of SEQ ID NO: 37, and a linker joining the two regions.

By way of further illustration, such a peptide or peptidomimetic can comprise SEQ ID NO: 38, which is a synthetic fluorescent derivative of IL-10 helix F. If the peptide or peptidomimetic is a dimeric compound, each region can comprise the sequence of SEQ ID NO: 38, and a linker joining the two regions.

TABLE 3

| Compound | Sequence | SEQ ID |
|---|---|---|
| IL10-HF-6 | Ac-C(Fluo)YKAx⁴SEFDIFINYIEAYx¹⁸Tx²⁰KIRN-NH₂ | 38 | x residues = norleucine

According to one aspect of the invention, the peptide or peptidomimetic comprises the amino acid sequence of the second helix of STAT3 or variant thereof. The peptide or peptidomimetic preferably binds at least to STAT3, although it may also bind to other STAT proteins. By way of illustration, SEQ ID NOs: 39-46 (inverse sequences) are based upon the second helix of STAT3, but incorporate several positions of variability indicated by an "X" in the sequence. The positions of the sequence indicated by an "X" can be substituted with any amino acid residue, provided that it does not eliminate the ability of the peptide or peptidomimetic to bind to a STAT protein, particularly STAT3, and/or inhibit the function of such protein. Table 4 illustrates preferred amino acids to be used at each position of variability represented by an "X". Of course, other amino acid residues can be used instead of the exemplary residues, which are provided for illustration, particularly amino acid residues having chemical properties similar to those of the exemplary residues. Thus, according to this aspect of the invention, the peptide or peptidomimetic can comprise the amino acid sequence of any of SEQ ID NOs: 39-42, or the inverse sequence thereof (e.g., SEQ ID NOs: 43-46). Specific examples of such sequences are provided by SEQ ID NOs: 47-76. As noted above, the peptide-based inhibitor preferably is a non-naturally occurring peptide or peptidomimetic.

TABLE 4

Xaa-Thr-Xaa-Tyr-Leu-Xaa-Xaa-Leu-His-Xaa-Leu-Xaa
(SEQ ID NO: 39)

Xaa-Thr-Arg-Tyr-Leu-Xaa-Gln-Leu-His-Lys-Leu-Tyr
(SEQ ID NO: 40)

Xaa-Thr-Xaa-Tyr-Leu-Xaa-Xaa-Leu-His-Xaa-Leu-Xaa-Xaa
(SEQ ID NO: 41)

Xaa-Thr-Arg-Tyr-Leu-Xaa-Gln-Leu-His-Lys-Leu-Tyr-Xaa
(SEQ ID NO: 42)

| Xaa Position (as applicable) | Preferred Amino Acids |
|---|---|
| 1 | Small amino acids*; Asp, Ala, or Asn |
| 3 | Positively charged amino acids; Arg or Lys |
| 6 | Polar amino acids; neutral and/or negatively charged amino acids; Glu or Gln |
| 7 | Polar amino acids; neutral and/or negatively charged amino acids; Glu or Gln |
| 10 | Positively charged amino acids; Gln, Lys, Diaminobutyric acid (Dab), Ala, or Glu |
| 12 | Aromatic amino acids; Tyr or CyPhen |
| 13 | Positively charged amino acids; Lys, Arg, or Ser |

¹-Xaa-Leu-Xaa-His-Leu-Xaa-Xaa-Leu-Tyr-Xaa-Thr-Xaa
(SEQ ID NO: 43)

¹-Tyr-Leu-Lys-His-Leu-Gln-Xaa-Leu-Tyr-Arg-Thr-Xaa
(SEQ ID NO: 44)

Xaa-Xaa-Leu-Xaa-His-Leu-Xaa-Xaa-Leu-Tyr-Xaa-Thr-Xaa
(SEQ ID NO: 45)

Xaa-Tyr-Leu-Lys-His-Leu-Gln-Xaa-Leu-Tyr-Arg-Thr-Xaa
(SEQ ID NO: 46)

| Xaa Position (as applicable) | Preferred Amino Acids |
|---|---|
| 1 | Positively charged amino acids; Lys, Arg, or Ser |
| 2 | Aromatic amino acids; Tyr or CyPhen |
| 4 | Positively charged amino acid, Gln, Lys, Diaminobutyric acid (Dab), Ala, or Glu |

TABLE 4-continued

| | |
|---|---|
| 7 | Polar amino acids; neutral and/or negatively charged amino acids; Glu or Gln |
| 8 | Polar amino acids; neutral and/or negatively charged amino acids; Glu or Gln |
| 11 | Positively charged amino acids; Arg or Lys |
| 13 | Small amino acids*; Asp, Ala, or Asn |

†An amino acid at position 1 of SEQ ID NOs: 43 and 44 is not required.
*Molecular mass of about 133 or less.

TABLE 5

| Compound | SEQ ID NO | Sequence |
|---|---|---|
| Hel2-Pen | 47 | LDTRYLEQLHQLYS |
| Hel2A-Pen | 48 | DTRYLEQLHKLYS |
| Hel2B-Pen | 49 | LDTRYLEQLHKLYS |
| Hel2C-Pen | 50 | DTRYLEQLHKLCyPheS |
| Hel2D-Pen | 51 | DTKYLEQLHKLYS |
| Hel2E-Pen | 52 | DTRYLQELHKLYS |
| Hel2F-Pen | 53 | DTRYLEQLHDabLYS |
| Hel2G-Pen | 54 | AQWNQLQQLDTRYLEQLHQLYS |
| Hel2A-2-Pen | 55 | LDTRYLEQLHKLY |
| Hel2A-2a-Pen | 56 | DTRYLEQLHKLY |
| Ac-Hel2A-2a-Pen | 57 | Ac-DTRYLEQLHKLY |
| Hel2H-Pen | 58 | LDTRYLEQLHDabLY |
| Hel2I-Pen | 59 | DTRYLEQLHDabLY |
| Hel2K-Pen | 60 | LDTKYLEQLHDabLY |
| Hel2A-3-Pen | 61 | Ac-DTRYLEQLHALY |
| Hel2A-4-Pen | 62 | Ac-DTRYLEQLHELY |
| Hel2A-5-Pen | 63 | Ac-ATRYLEQLHKLY |
| ST3-H2a-K-Pal | 64 | DTKYLEQLHKLYKK-ε-Pal |
| St3-Hel2A-2 (ST3-H2A2) | 65 | LDTRYLEQLHKLY |

*CyPhe refers to 4-cyano phenylalanine

TABLE 6

| Compound | Sequence ID No. | Sequence |
|---|---|---|
| St3-H2a-2a-Pal1 | 66 | Pal-IQRYLKHLQELYRTD (all-D) |
| St3-H2a-2a-Pal2 | 67 | Pal-IQKYLKHLQELYRTD (all-D) |
| St3-H2a-2a-Pal3 | 68 | Pal-QRYLKHLQELYRTD (all-D) |
| St3-H2a-2a-Pal4 | 69 | Pal-RYLKHLQELYRTD (all-D) |
| St3-H2a-2a-Pal6 | 70 | Pal-QKYLKHLQELYRTD (all-D) |
| St3-H2a-2a-Pal7 | 71 | Pal-KYLKHLQELYRTD (all-D) |
| St3-H2a-2a-Pal8 | 72 | Pal-IQRYLKHLQQLYRTD (all-D) |
| St3-H2a-2a-Pal9 | 73 | Pal-IQRYLKHLQQLYRTN (all-D) |
| St3-H2a-2a-Pal10 | 74 | Pal-YLKHLQELYRTD (all-D) |
| St3-H2a-2a-Pal11 | 75 | Pal-QRYLKHLQELYRTDL (all-D) |
| St3-H2a-2a-Pal12 | 76 | Pal-YLKHLQQLYRTN (all-D) |

The peptide or peptidomimetic can comprise the inverse sequence of any of the sequences described herein. Furthermore, any of the foregoing sequences can be cyclized by known methods. For instance, cysteine, lysine, and/or glutamic acid residues can be introduced at desired positions of cyclization.

Variant sequences other than those specifically mentioned herein are contemplated, which comprise significant sequence identity to the disclosed amino acid sequences (e.g., 80%, 85%, 90%, 95%, 98%, or 99% sequence identity) and retain the ability to inhibit cytokine signaling and/or STAT protein activation. Such variants comprise one or more amino acid substitutions, deletions, or insertions as compared to the parent amino acid sequence. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc. In one embodiment, the peptide-based inhibitor of IL-10 has at least 90% (e.g., at least 95%, at least 98%, or at least 99%) identity to SEQ ID NOs: 1-38 or the inverse sequence thereof. In another embodiment, the peptide-based inhibitor of STAT3 has at least 90% (e.g., at least 95%, at least 98%, or at least 99%) identity to SEQ ID NOs: 39-76 or the inverse sequence thereof.

The peptide or peptidomimetic also can comprise synthetic, non-naturally occurring amino acids. Such synthetic amino acids include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The term "peptidomimetic" as used herein refers to a compound that comprises the same general structure of a corresponding polypeptide, but which includes modifications that increase its stability or biological function. For instance, the peptidomimetic can be a "reverso" analogue of a given peptide, which means that the peptidomimetic comprises the reverse sequence of the peptide. In addition, or instead, the peptidomimetic can comprise one or more amino acids in a "D" configuration (e.g., D-amino acids), providing an "inverso" analogue. Peptidomimetics also include peptoids, wherein the side chain of each amino acid is appended to the nitrogen atom of the amino acid as opposed to the alpha carbon. Peptoids can, thus, be considered as N-substituted glycines which have repeating units of the general structure of $NRCH_2CO$ and which have the same or substantially the same amino acid sequence as the corresponding polypeptide.

The peptide or peptidomimetic can comprise the indicated amino acid sequence(s) alone or as part of a larger sequence, which includes additional amino acid residues (e.g., one, two, three, four, five or more amino acid residues) flanking the indicated amino acid sequence to the amino-terminal side, carboxy-terminal side, or both. Any flanking sequences can be used, provided the additional amino acid sequences do not eliminate the ability of the peptide to inhibit cytokine signaling, STAT activation, STAT function, and/or STAT signaling. Thus, for example, the peptide or peptidomimetic can comprise flanking sequences from the native molecule that the peptide or peptidomimetic is designed to mimic, in which case the flanking sequences, alone or together with the sequences specifically indicated herein, comprise a fragment of the native molecule (e.g., IL10R1, IL10R2, IL10, or STAT3).

The peptide or peptidomimetic can comprise, consist essentially of, or consist of, any of foregoing sequences or variants thereof. The peptide or peptidomimetic consists essentially of the foregoing sequences if it does not comprise other elements that prevent the peptide from inhibiting cytokine signaling, STAT activation, STAT function, and/or STAT signaling.

Smaller peptides and peptidomimetics are believed to be advantageous for inhibition and to facilitate entry into a cell. Thus, the peptide or peptidomimetic preferably comprises fewer than about 40 amino acids, such as about 35 or fewer amino acids, about 25 or fewer amino acids, or even about 20 or fewer amino acids. Generally, however, the peptide or peptidomimetic will comprise at least about 8 amino acids, such as at least about 10 amino acids, or at least about 15 amino acids.

The peptide or peptidomimetic can be used alone, or it can be coupled to a peptide stabilizing motif that stabilizes the folding of the peptide, or a cell penetrating motif so as to more efficiently facilitate the delivery of the peptide to the interior of a cell. Thus, the peptide or peptidomimetic can be provided as part of a composition comprising the peptide and a peptide stabilizing or cell penetrating motif. Any of various peptide stabilizing or cell penetrating motifs known in the art can be used, such as lipids and fatty acids, peptide transduction domains (e.g., HIV-TAT, HSV Transcription Factor (VP22), and penetratin), and other types of carrier molecules (e.g., Pep-1).

According to one aspect of the invention, the peptide stabilizing or cell penetrating motif is a fatty acid or lipid molecule. The fatty acid or lipid molecule can be, for example, a palmitoyl group, farnesyl group (e.g., farnesyl diphosphate), a geranylgeranyl group (e.g., geranylgeranyl diphosphate), a phospholipid group, glycophosphatidylinositol, phosphatidylserine, phosphatidylethanolamine, sphingomyelin, phosphatidylcholine, cardiolipin, phosphatidylinositol, phosphatidic acid, lysophosphoglyceride, a cholesterol group, an acetyl group, and the like. Preferably, the fatty acid molecule is a $C_1$ to $C_{24}$ fatty acid, e.g., lauric acid, palmitic acid, myristic acid, stearic acid, oleic acid, linoleic acid, α-linoleic acid, linolenic acid, arachidonic acid, timnodonic acid, docosohexenoic acid, erucic acid, arachidic acid, behenic acid. More preferably, the fatty acid molecule is a $C_8$ to $C_{16}$ fatty acid.

The fatty acid or lipid molecule can be attached to any suitable part of the peptide or peptidomimetic. In a preferred embodiment of the invention, the fatty acid or lipid molecule is attached at the amino (N-) terminus, the carboxyl (C-) terminus, or both the N- and C-termini of the peptide or peptidomimetic. When the fatty acid or lipid molecule is attached at the C-terminus of the polypeptide or peptidomimetic, the fatty acid or lipid molecule preferably is modified, e.g., to include an amino group such as $NH_2(CH_2)_n$—COOH or $CH_3(CH_2)_mCH(NH_2)COOH$, wherein each of n and m is, independently, 1 to 24, preferably 8 to 16. The fatty acid or lipid residue can advantageously be attached to a terminal lysine in the epsilon (ε) position.

According to another aspect of the invention, the cell penetrating motif is a peptide transduction domain (also known as protein transduction domains or PTDs). PTDs typically are fused to the STAT-inhibitory peptide or peptidomimetic. Thus, the peptide or peptidomimetic can be a fusion protein comprising the peptide or peptidomimetic and a PTD. Often, the fusion protein is cleaved inside of a cell to remove the cell penetrating motif.

The peptide or peptidomimetic can further comprise linking residues disposed between the amino acid sequence and the peptide stabilizing or cell penetrating motif. Illustrative examples of such linking residues include K, KK, RK, RQ, KQ, RQI, KQI, RQIK (SEQ ID NO: 77), and KQIK (SEQ ID NO: 78).

The peptide or peptidomimetic can be prepared by any method, such as by synthesizing the peptide or peptidomimetic, or by expressing a nucleic acid encoding an appropriate amino acid sequence in a cell and harvesting the peptide from the cell. Of course, a combination of such methods also can be used. Methods of de novo synthesizing peptides and peptidomimetics, and methods of recombinantly producing peptides and peptidomimetics are known in the art (see, e.g., Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, N Y, 1994).

Nucleic acids encoding the amino acid sequence of the peptide or peptidomimetic can comprise DNA (e.g., cDNA) or RNA, and can be single or double stranded. Furthermore, the nucleic acid can comprise nucleotide analogues or derivatives (e.g., inosine or phophorothioate nucleotides and the like). The nucleic acid can encode the amino acid sequence of the peptide or peptidomimetic alone, or as part of a fusion protein comprising such sequence and a cell penetrating motif, as described herein. The nucleic acid encoding the amino acid sequence of the peptide or peptidomimetic can be provided as part of a construct comprising the nucleic acid and elements that enable delivery of the nucleic acid to a cell, and/or expression of the nucleic acid in a cell. Such elements include, for example, expression vectors and transcription and/or translation sequences. Suitable vectors, transcription/translation sequences, and other elements, as well as methods of preparing such nucleic acids and constructs, are known in the art (e.g., Sambrook et al., supra; and Ausubel et al., supra).

The peptide or peptidomimetic and nucleic acid (e.g., recombinant DNA or cDNA) preferably are non-naturally occurring. In one embodiment, the peptide or peptidomimetic or nucleic acid are "isolated," which encompasses compounds or compositions that have been removed from a biological environment (e.g., a cell, tissue, culture medium, body fluid, etc.), or otherwise increased in purity to any degree (e.g., isolated from a synthesis medium). Isolated compounds and compositions, thus, can be synthetic or naturally produced.

A cell comprising the peptide or peptidomimetic, or nucleic acid encoding the amino acid sequence of the peptide or peptidomimetic, includes, for example, a cell engineered to express a nucleic acid encoding the amino acid sequence of the peptide or peptidomimetic. Suitable cells include prokaryotic and eukaryotic cells, e.g., mammalian cells, yeast, fungi, and bacteria (such as *E. coli*). The cell can be in vitro, as is useful for research or for production of the peptide or peptidomimetic, or the cell can be in vivo, for example, in a transgenic mammal that expresses the peptide.

The peptide or peptidomimetic can be administered to the cell by any method. For example, the peptide or peptidomimetic can be administered to a cell by contacting the cell with the peptide or peptidomimetic, typically in conjunction with a regent or other technique (e.g., microinjection or electroporation) that facilitates cellular uptake. Alternatively, and preferably, the peptide or peptidomimetic is administered by contacting the cell with a composition comprising the peptide or peptidomimetic and a cell penetrating motif, as discussed herein.

Alternatively, the peptide or peptidomimetic can be administered by introducing a nucleic acid encoding the amino acid sequence of the peptide or peptidomimetic into the cell such that the cell expresses a peptide comprising the amino acid sequence. The nucleic acid encoding the peptide or peptidomimetic can be introduced into the cell by any of various techniques, such as by contacting the cell with the nucleic acid or a composition comprising the nucleic acid as part of a construct, as described herein, that enables the delivery and expression of the nucleic acid. Specific protocols for introducing and expressing nucleic acids in cells are known in the art (see, e.g., Sambrook et al. (eds.), supra; and Ausubel et al., supra).

The peptide, peptidomimetic, or nucleic acid can be administered to a cell in vivo by administering the peptide, peptidomimetic, nucleic acid, or pharmaceutical composition comprising the peptide, peptidomimetic, or nucleic acid to a host comprising the cell. The host can be any host, such as a mammal, preferably a human. Suitable methods of administering peptides, peptidomimetics, and nucleic acids to hosts are known in the art, and discussed in greater detail in connection with the pharmaceutical composition, below.

Any one or more of the compounds or compositions of the invention described herein (e.g., peptide or peptidomimetic, nucleic acid, or cell) can be formulated as a pharmaceutical composition comprising a compound of the invention and a pharmaceutically acceptable carrier. Furthermore, the compounds or compositions of the invention can be used in the methods described herein alone or as part of a pharmaceutical formulation.

The pharmaceutical composition can comprise more than one (e.g., two, three, four, five, or more) compound (e.g., peptide or peptidomimetic, nucleic acid, or cell) or composition of the invention. Alternatively, or in addition, the pharmaceutical composition can comprise one or more (e.g., two, three, four, five, or more) other pharmaceutically active agents or drugs.

In one embodiment, one or more (e.g., two, three, four, five, or more) peptides or peptidomimetics can be administered (e.g., in a composition) with a vaccine to promote an immune response against an infectious disease. Although not wishing to be bound by any particular theory, the peptide or peptidomimetic may have an adjuvant effect when administered with a vaccine.

Vaccines for infectious diseases include, but are not limited to, vaccines for chickenpox, diphtheria, hepatitis A, hepatitis B, haemophilis influenza type b, human papillomavirus, influenza, Japanese encephalitis, measles, meningococcal, mumps, pertussis, pneumococcal, polio, rabies, rotavirus, rubella, shingles, tetanus, tuberculosis, typhoid fever, or yellow fever.

The carrier can be any of those conventionally used and is limited only by physio-chemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular compound or composition of the invention and other active agents or drugs used, as well as by the particular method used to administer the compound and/or inhibitor. Accordingly, there are a variety of suitable formulations of the pharmaceutical composition of the present inventive methods. The following formulations for oral, aerosol, parenteral, subcutaneous, intravenous, intramuscular, interperitoneal, rectal, and vaginal administration are exemplary and are in no way limiting. One skilled in the art will appreciate that these routes of administering the compound of the invention are known, and, although more than one route can be used to administer a particular compound, a particular route can provide a more immediate and more effective response than another route. In a preferred embodiment, the compound of the invention is administered as an inhalant. Localized treatment (e.g., as an inhalant) is preferred since conventional systemic treatment (e.g., of system IFN-γ) can have negative side effects.

The peptide, peptidomimetic, nucleic acid, cell, or composition can be administered in any suitable amount. In one embodiment, a therapeutically effective amount or pharmaceutically effective amount of the compounds or compositions of the invention is administered. By "therapeutically effective amount" or "pharmaceutically effective amount" is meant a compound or composition, as disclosed for this invention, which has a therapeutic effect. The doses of the compounds or compositions which are useful in treatment are therapeutically effective amounts. Thus, as used herein, a therapeutically effective amount means those amounts of the compounds or compositions that produce the desired therapeutic effect as judged by clinical trial results and/or model animal infection studies. In particular embodiments, the compounds or compositions are administered in a predetermined dose and, thus, a therapeutically effective amount would be an amount of the dose administered. This amount and the amount of the compounds or compositions can be routinely determined by one of skill in the art, and will vary, depending on several factors, such as the patient's height, weight, sex, age, and medical history. For prophylactic treatments, a therapeutically effective amount is that amount which would be effective to prevent a microbial infection.

A "therapeutic effect" relieves, to some extent, one or more of the symptoms of the infection, and includes curing an infection. "Curing" means that the symptoms of active infection are eliminated, including the total or substantial elimination of excessive members of viable microbe of those involved in the infection to a point at or below the threshold of detection by traditional measurements. However, certain long-term or permanent effects of the acute or chronic infection may exist even after a cure is obtained (such as extensive tissue damage). As used herein, a "therapeutic effect" is defined as a statistically significant reduction in bacterial load in a host, emergence of resistance, pulmonary function, or improvement in infection symptoms or functional status as measured by human clinical results or animal studies.

"Treat," "treatment," or "treating," as used herein refers to administering a pharmaceutical composition for prophylactic and/or therapeutic purposes. The term "prophylactic treatment" refers to treating a patient who is not yet infected, but who is susceptible to, or otherwise at risk of, a particular infection such that there is a reduced onset of infection. The term "therapeutic treatment" refers to administering treatment to a patient already suffering from an infection that may be acute or chronic. Treatment may eliminate the pathogen, or it may reduce the pathogen load in the tissues that results in improvements measured by the patient's symptoms or measures of lung function. Thus, in preferred embodiments, treating is the administration to a patient (either for therapeutic or prophylactic purposes) of therapeutically effective amounts of a compound or composition of the invention.

The peptide-based inhibitor of the STAT3-IL10 signaling pathway can be administered in further combination with other TB therapies (e.g., antibiotics). For example, the peptide-based inhibitor can be administered sequentially or simultaneously with other TB therapies (e.g., isoniazid, rifampin, pyrazinamide, ethambutol, and/or streptomycin).

Injectable formulations are among those formulations that are preferred in accordance with the present invention. The requirements for effective pharmaceutical carriers for injectable compositions are well-known to those of ordinary skill in the art (See, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

Topical formulations are well-known to those of skill in the art. Such formulations are particularly suitable in the context of the present invention for application to the skin.

Formulations suitable for oral administration can consist of (a) liquid solutions, such as an effective amount of the inhibitor dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compounds and compositions of the invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compounds and compositions of the invention can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-b-aminopropionates, and 2-alkyl-imidazoline quaternary ammonium salts, and (e) mixtures thereof.

Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the compounds of the invention, or compositions comprising such compounds, can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

The following examples further illustrate the invention but, of course, should not be construed as in any way limiting its scope.

Example 1

This example demonstrates describes the materials and methods for the remaining Examples set forth herein.

Mice and Experimental Infection

Six to eight weeks old C57BL/6 female mice were purchased from Jackson (Bar Harbor, Me.). The IACUC of Colorado State University approved all animal procedures used in this study. The mice were kept in sterile condition in BSL3 facilities and they were rested for a week prior to infection. The mice were then infected with a low dose aerosol infection using the Glass-Col System to deliver ~50-100 *Mycobacterium tuberculosis* (Mtb) (Erdman strain, TMC107; ATCC 35801) bacilli per mouse.

Bacterial deposition in the lungs after aerosol was assessed by sacrificing three mice at day 1 post-infection and determining bacterial load as follows. Following euthanasia, mouse tissues (lung and spleen) were homogenized using the Next Advance Bullet Blender (Averill Park, N.Y.). Briefly, the left lobe of the lung or spleen was placed in a 1.5 ml sterile, safe lock Eppendorf tube containing 0.5 ml of sterile saline and 3×3.2 mm, sterile stainless steel beads, and thereafter the tubes were placed in the Bullet Blender and homogenized during 4 min and 8000 rpm. The bacterial load was determined using serial dilutions of homogenized organs that were plated on 7H11 agar plates and the colony forming units (CFU) in each sample were determined after 3 weeks of incubation at 37° C. Bacterial load in each animal and organ was expressed as the $\log_{10}$ of CFUs.

Peptide Inhibitors

Peptides were synthesized by microwave-assisted solid phase synthesis on Liberty peptides synthesizer (CEM Corporation) using Fmoc chemistry as described in Johannessen et al., *Chembiochem: a European Journal of Chemical Biology*, 12: 914-921 (2011). Mice were treated with ST3-H2A2, IL10R1-7, and IL10R1-14 peptide inhibitors as follows. The mice received six doses during two weeks of 100 µg/50 µl of 0.9% saline (low endotoxin) per mouse/dose (Experiment 1) or 50 µg/50 µl of 0.9% saline (low endotoxin) per mouse/dose (Experiment 2) of ST3-H2A2, IL10R1-7, and IL10R1-14 peptide inhibitors via intrapulmonary aerosol delivery.

Intrapulmonary Aerosol Delivery

Mice received the drugs by intrapulmonary aerosol delivery using a MicroSprayer™ device (MicroSprayer™ model IA-C; Penn Century, Philadelphia, Pa.) attached to an FMJ-250 high pressure-syringe device (Penn Century) as described in De Groote et al., *The Journal of Antimicrobial Chemotherapy*, 69: 1057-1064 (2014); Gonzalez-Juarrero et al., *Antimicrob. Agents Chemother.*, 56: 3957-3959 (2012); Higgins et al., *Tuberculosis*, 89: 149-157 (2009); Lee et al., *Nature Medicine*, 20: 152-158 (2014); Rosas-Taraco et al., *American Journal of Respiratory Cell and Molecular Biology*, 41: 136-145 (2009); and Rosas-Taraco et al., *Tuberculosis*, 91: 98-106 (2011).

Briefly, mice were anesthetized using isoflurane and oxygen mix (5% isoflurane in oxygen 4 L/min; VIP 3000 isoflurane vaporizer) for about 10 minutes until animals were sedated. Each mouse was placed on its abdomen in a Perspex support adjusted to 45° angle, the teeth were suspended up with an incisor loop located on top. The mouth was opened and, with the help of a cotton tip, the tongue was pulled out. Then, the MicroSprayer™ tip was aimed and introduced into the trachea until reaching the carina and the formulation was sprayed. The mouse was then taken off from the Perspex support and laid in its cage until it awoke from the anesthesia (2-3 minutes). After administration of the anesthetic, the animals were monitored for regular breathing and clinical symptoms. Mice were monitored on a daily basis and their weights recorded.

Protein Quantification

Lung lysates were centrifuged at 4° C. for 10 minute at 2,000 rpm to remove debris and supernatants were quantified for total protein concentration using the BCA assay (Pierce, Rockford, Ill.) and following the manufacturer's recommendations.

Lung homogenates were screened for pSTAT3 (pY705 (tyrosine 705)) by ELISA following manufacturer's recommendations (Life Technologies). Briefly, the lung homogenates were re-suspended in the cell extraction buffer and incubated during 30 minutes on ice with intermittent vortexing followed by pelleting of the cell debris. Supernatants from each sample were collected and screened for their content of STAT3 (pY705). Standards were prepared using purified recombinant phosphorylated STAT3 protein. Thereafter, 100 μl of standards and diluted samples or control aliquots were distributed into microtiter wells and were incubated in the wells pre-coated with anti-pSTAT3 antibody. The reactions were developed using the detection anti-pSTAT3 antibody followed by 30 minutes incubation at RT with anti-rabbit IgG HRP. The reactions were visualized by incubation with a chromogenic substrate of HRP during 30 minutes at room temperature. The reactions were stopped with 100 μl of stop solution added to each well. Absorbance for each well was read at 450 nm.

Real Time PCR

The upper right lobe of the lungs from each mouse were homogenized in Trizol (Invitrogen) using Next Advance bullet blender (Averill Park, N.Y.) and frozen at −80° C. immediately. RNA was extracted following the manufacturer's protocol. Trizol DNA was digested with RQ1 RNase-free DNase (Promega, Madison, Wis.) and RNA was re-isolated using Trizol. Finally, the concentration of RNA in each sample was measured by spectrophotometry and the RNA was reverse transcribed with M-Mulv (New England Bio Labs, Ipswich, Mass.) and random hexamers (Roche, Basel, Switzerland).

Real-time PCR was performed using 5 μl of cDNA and Platinum SYBR Green qPCR SuperMix-UDG (Invitrogen) in iQ5 thermo cycler (Bio-Rad, Hercules, Calif.) to evaluate relative mRNA expression of IL-10, STAT3, IFNγ, iNOS, and Arg-1. 18s was used to normalize the expression levels.

Primer sequences used were:

```
IL-10 forward primer
                                        (SEQ ID NO: 79)
5' GCTCTTACTGACTGGCATGAG 3'
and reverse primer
                                        (SEQ ID NO: 80)
5' CAA TACCATTGACCTGCCGAT 3';

STAT3 forward primer
                                        (SEQ ID NO: 81)
5' AATACCATTGACCT GCCGAT 3'
and reverse primer
                                        (SEQ ID NO: 82)
5' AGCGACTCAAACTGCCCT 3';

IFNγ forward primer
                                        (SEQ ID NO: 83)
5' ATGAACGCTACACACTGCATC 3'
and reverse primer
                                        (SEQ ID NO: 84)
5' CCATCCTTTTGCCAGTTCCTC 3';

iNOS forward primer
                                        (SEQ ID NO: 85)
5' GTTCTCAGCCCAACA ATACAAGA 3'
and reverse primer
                                        (SEQ ID NO: 86)
5' GTGGACGGGTCGATGTCA C 3'
```

```
Arg-1 forward primer
                                        (SEQ ID NO: 87)
5' CAGAAGAATGGAAGAGTCAG 3'
and reverse primer
                                        (SEQ ID NO: 88)
5' CAGATATGCAGGGAG TCACC 3';

18S forward primer
                                        (SEQ ID NO: 89)
5' GTAACCCGTTGAACCCCATT
and the reverse primer
                                        (SEQ ID NO: 90)
5' CCATCCAATCGGTAGTAGCG 3'.
```

Amplification conditions were as follows: 95° C. for 3 min, 95° C. for 10 sec, denaturation annealing and extension at 60° C. for 30 sec for 40 cycles followed by 95° C. for 10 sec. Specificity was verified by melt-curve analysis by an increment of 0.5° C. at 0.05 min rate from 60° C. to 95° C. iNOS mRNA levels were normalized with 18s levels using the comparative Ct (ΔΔCt) method to calculate relative changes. The 18s rRNA was used as housekeeping gene. The fold induction of Il-10 or Stat3 transcripts in RNA from lung samples was measured as fold induction of Stat3 or Il-10 in samples from Mtb infected mice relative to the same transcript levels of expression in samples obtained from the lungs of naïve mice. The percentage of inhibition for each transcript in each sample obtained from Mtb infected mice after peptide treatment was determined relative to the expression of the same targeted gene in similar samples obtained from untreated mice.

Histopathology Analysis

The diaphragmatic lobe of the lungs of each mouse was placed into histology cassette and fixed in 4% paraformaldehyde. Samples were inactivated in the 4% paraformaldehyde solution during 48 hrs inside the BSL3 facility and then processed using standard histological protocols.

Immunohistochemistry

Paraffin embedded blocks from each group of mice were cut in sections of 5-7 μm using a microtome and placed onto slides. Thereafter, the paraffin was removed from the tissue sections using Histo-Clear (Electron Microscopy Sciences, Hatfield, Pa.). Following this step and tissue rehydration, endogenous tissue peroxidase was blocked using Peroxidase 1 (Biocare, Calif.) for 5 min at room temperature. Thereafter, the sections were treated with a citrate buffer from Dako Inc. (Carpinteria, Calif.) and pressure cooker standard procedure for antigen retrieval. The unspecific binding of antibodies was blocked by incubating the sections for 5 minutes at room temperature with Background Sniper (Biocare, Calif.) and then each section was incubated overnight at room temperature with a primary antibody raised against murine pSTAT3 (mouse monoclonal IgG1 sc-81523 from Santa Cruz Biotechnology) and IL-10 (Purified anti-mouse IL-10, Cat No. 16-7102-81, eBioscience) antigens.

Cell permeability preceded the pSTAT3 staining by incubation with ice-cold methanol during 20 minutes. When the host of the primary antibody was a mouse, then unspecific binding to mouse tissue was blocked using the Mouse on Mouse kit (Vector Laboratories, CA) as per manufacturer's instructions. After washing the slides three times for 5 min in PBS at room temperature, the slides were incubated again with the appropriate secondary antibody for 60 minutes at room temperature. Slides were washed and incubated again for 15 minutes with the ImmPACT® DAB or AEC peroxidase substrate (Impact AEC or DAB; Vector Lab, MI). In some instances after the ImmPACT® DAB incubation, the slides were processed for acid fast staining using BD TB carbofuchsin KF during 30 minutes at room temperature followed by acid-alcohol washes. Finally the slides were counterstained by immersing the sections for 1 min in haematoxylin 560 (SURGIPAD, Leica Microsystem) and mounted for microscopic observation using Super Mount permanent mounting media (Aqueous) (Biogenex, Fremont, Calif.)). As a negative control, the procedure described above was also carried out omitting the primary antibody step. Sections were examined using an Olympus X70 microscope.

Cytometric Bead Array (CBA) Analysis

The lung homogenates were analyzed using the CBA Kit from BD Biosciences (Franklin Lakes, N.J.), which analyzed IL-6, IL-10, IL-12, TNF-α, IFNγ, and MCP-1. Prior to analysis and inside the BSL3 facilities, the samples were thawed at 4° C. and centrifuged at 8000 rpm to remove all sediments. At the end of the CBA, samples were decontaminated by fixation with 100 μl of 4% PFA per sample and incubation at 4° C. for at least 24 hrs. Thereafter, the samples were read using a FACsCanto by using BD Biosciences CBA software (Das). Cytokine levels in each sample were calculated by extrapolating the mean fluorescence intensity (MFI) for each sample into the standard curves for every cytokine.

Antimicrobial Products

The quantification of end effector molecules and enzymes involved in the host antimicrobial activity in the lungs of mice were performed using lung homogenates obtained as indicated above. Lung homogenate supernatants were used in a Griess reaction (G 7921, Molecular probes, Invitrogen, Eugene, Oreg.), Arginase assay (Bioassay Systems, DARG-200), NADPH (Bioassay Systems, ECNP-100), and lysozyme (Molecular Probes E-22013).

For the Griess reaction, reagents were acclimated at room temperature for 20 min prior to the assay. Thereafter, the samples were centrifuged at 1200 rpm for 2 min and the Griess reaction was performed following the manufacturer's instructions. Briefly, samples and prepared standards were diluted following the manufacturer's instructions with distilled sterile water in a 96 well plate. 20 μl of Griess reaction were added to each reaction well. Samples and standards were incubated for 30 minutes in the dark. Thereafter, samples were read using a Biotech Synergy 2 Multi-Mode Micro Plate Reader [U5] spectrophotometer at 546 nm.

For the NADPH assay, each lung homogenate was mixed in a 1.5 mL Eppendorf tube with 100 μL NADPH extraction buffer for NADPH determination. Extracts then were heated at 60° C. for 5 min and then 20 μl assay buffer and 100 μl of the opposite extraction buffer were added to neutralize the extracts. Samples were briefly vortexed and centrifuged at 13,000 rpm for 5 min. The resulting supernatant was used for NADPH assays. 40 μl of standards were then transferred into wells of a clear bottom 96-well plate. For each well of the reaction, 80 μL working reagent were added per well quickly. Optical density for time "zero" (OD0) optical density after 30 min incubation (OD30) at room temperature were read at 565 nm (520-600 nm).

The Lysozyme assay was performed as per manufacturer's instructions. Briefly, experimental samples were first diluted in 1× reaction buffer. A volume of 50 μl was used for each reaction. Then, 50 μl of the 50 μg/ml DQ lysozyme substrate were added to each microplate well containing the experimental or the standard curve samples. The reaction mix was then incubated at 37° C. for 30 min protected from light. The fluorescence in each of the samples was measured at absorption maxima at ~494 nm and fluorescence emission maxima at ~518 nm.

The level of arginase activity in each lung homogenate was performed using the Quanti-Chrom Arginase Assay Kit (Bio Assay Systems, Hayward, Calif.). Briefly, protein concentration was normalized to 100 μg/ml. As a control, an aliquot of normalized protein was heat-inactivated at 90° C. for 10 min. 40 μl of untreated or heat-inactivated sample was incubated at 37° C. for 60 min with 10 μl of 5× reagent. Thereafter, the reaction was processed as recommended by the manufacturer and analyzed in a plate reader (Bio-Rad, Hercules, Calif.) at an absorbance of 430 nm. The absorbance of the heat-inactivated sample was subtracted from the respective untreated sample and then compared to urea standards. Activity of the arginase was reported in mU/mg of protein.

Statistical Analysis

The results are representative of two large trials. In experiment 1, the mice received six doses of the drugs during two weeks with 100 μg/50 μl per mouse/dose. In experiment 2, mice received six doses during two weeks with 50 μg/50 μl per mouse/dose of ST3-H2A2 (SEQ ID NO: 65), IL10R1-7 (SEQ ID NO: 31), and IL10R1-14 (SEQ ID NO: 11) peptide inhibitors.

The CFU results were obtained from samples obtained from experiments 1 and 2. The RT-PCR, antimicrobial end products, CBA, and histology were performed with samples obtained from experiment 1. For each experiment, the presented data use the mean values from 5 mice per group (except for mice treated with RF-4 where n was 4). Data are expressed as the mean±SEM values from triplicate assays. One-way analysis of variance and the Bonferroni's Multiple Comparison Test was used for analyzing the p value by comparing all the groups to each other at the confidence interval of 95%. Calculations were performed using Graphpad Prism version 4.00 for Windows (San Diego Calif. USA). P-values<0.05 were considered significant.

Example 2

This example demonstrates the expression of STAT3 and IL-10 in the lungs of mice infected with *Mycobacterium tuberculosis* (Mtb).

Previous studies have reported the up-regulation of expression of IL-10 in the lungs of chronically Mtb infected (Beamer et al., *J. Immunol.*, 181, 5545-5550 (2008); Higgins et al., *J. Immunol.*, 180: 4892-4900 (2009); Ordway et al., *J. Immunol.*, 176: 4931-4939 (2006), Rosas-Taraco et al., *Tuberculosis*, 91: 98-106 (2011); Turner et al., *J. Immunol.*, 169: 6343-6351 (2002); and Turner et al., *Infection and Immunity*, 69: 3264-3270 (2001)). However, the expression of STAT3 or its phosphorylated form pSTAT3 in the lungs of mice chronically infected with Mtb has not been reported previously.

Figure 1B:
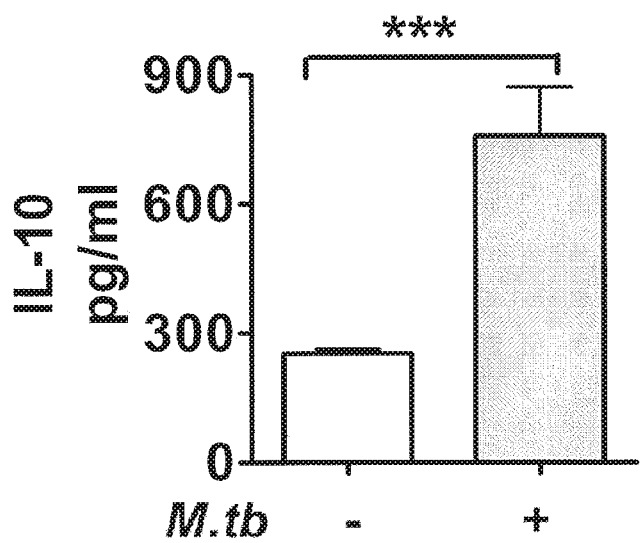

The expression of STAT3 and IL-10 in the lungs of mice with a chronic infection of Mtb was determined using ELISA, CBA and immunohistochemistry (IHC) to recognize pSTAT3 or IL-10 (FIGS. 1A and 1B) and via RT-PCR for transcripts of stat3 or il-10 (FIGS. 3A-3D). The results demonstrated that lung homogenates obtained from mice with 60 days of infection had increased levels of pSTAT3 and IL-10 expression (FIGS. 1A and 1B).

When lung tissue sections from similar mice with 60 days of infection with Mtb were analyzed by IHC, many macrophages and occasional foamy cells and lymphocytes located within the granulomatous lesion were found to be positive for expression of pSTAT3. pSTAT3 IHC followed by acid-fast bacilli (AFB) staining identified cells within the granulomatous lesions in which the pSTAT3 and AFB co-localized within the same cell. When stained for IL-10, similar tissue sections also appeared positive in macrophage and lymphocytes within the granuloma. Likewise, when staining for IL-10 by IHC was followed by AFB staining to visualize the Mtb bacilli within the lesions, it was revealed that IL-10 and AFB co-localize with the same cells.

Overall these results demonstrate that pSTAT3 and IL-10 are upregulated in cells located at the site of the lesions in the lungs of mice chronically infected with Mtb. Furthermore this analysis showed that some cells at the site of the lesions express high levels of pSTAT3 and IL-10 and co-localize with AFB positive staining.

Example 3

This example demonstrates the pulmonary bacterial load for mice treated with peptide inhibitors of STAT3 or IL-10.

The effect of pharmacological intervention with the IL-10-STAT3 signaling pathway in the pulmonary Mtb bacterial load for aerosolized Mtb-challenged mice was determined. The results demonstrated that the pulmonary bacterial load for mice treated with 6 doses of 100 µg/dose of ST3-H2A2 during a two week period had been reduced by 1.7 $\log_{10}$ CFU when compared to control untreated mice chronically infected with Mtb.

Figure 2A:
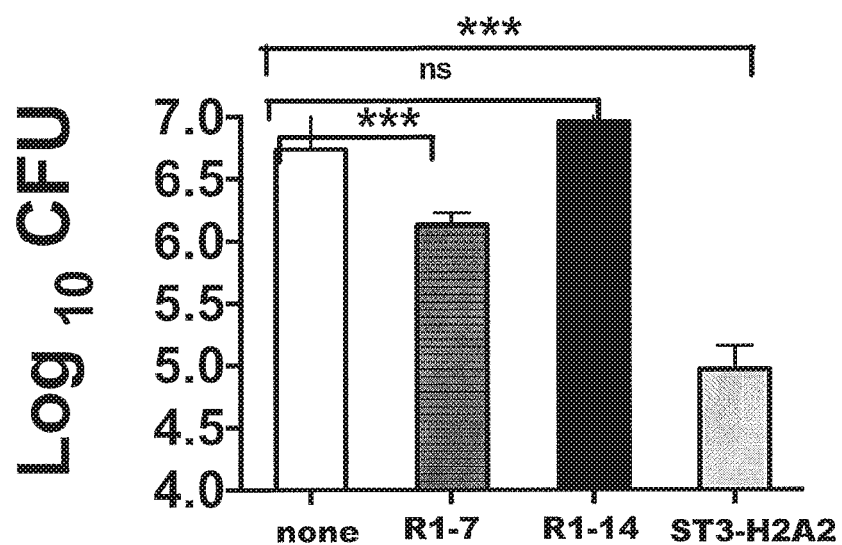
FIGS. 2A and 2B are tables illustrating pulmonary bacterial load after local pulmonary host directed therapy (HDT) with the peptide inhibitors IL10R1-7, IL10R1-14, and ST3-H2A2. Mice were infected with a low dose aerosol of *Mycobacterium tuberculosis* (Erdman) strain. Sixty days after the infection, mice were randomly assigned to groups. Each group of mice was either not treated or treated three times per week for two weeks via local intrapulmonary aerosol HDT with the peptides IL10R1-7, IL10R1-14, and ST3-H2A2. Twenty-four hours after the last dose, mice were euthanized and the lungs were harvested and prepared for bacterial load determination.

Treatment of chronically Mtb infected mice with the peptide inhibitor IL10R1-7 also decreased the pulmonary CFU by 0.6 $\log_{10}$ whereas similar treatments with the peptide inhibitor IL10R1-14 showed a slight increase in the pulmonary CFU (FIG. 2A). Likewise the splenic bacilli load was reduced by 0.9 $\log_{10}$CFU only in mice treated with ST3-H2A2.

Figure 2B:
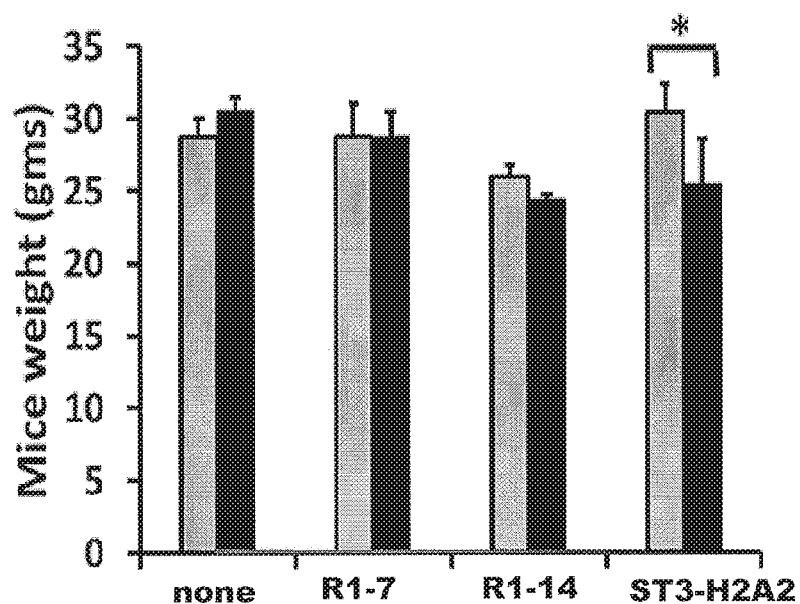

During treatment, mice generally did not show adverse effects except that mice treated for two weeks with peptide inhibitor ST3-H2A2 experienced mild weight loss (FIG. 2B). In a separate experiment when chronically Mtb infected mice were treated with a lower 50 µg/dose of ST3-H2A2, IL10R1-7, or IL10R1-14, only the group of mice receiving the peptide inhibitor ST3-H2A2 had reduced the pulmonary CFU (by 0.6 $\log_{10}$) when compared to control untreated mice chronically infected with Mtb. No changes in the bacterial load of the spleen were observed with this therapy.

Example 4

Figure 3A:
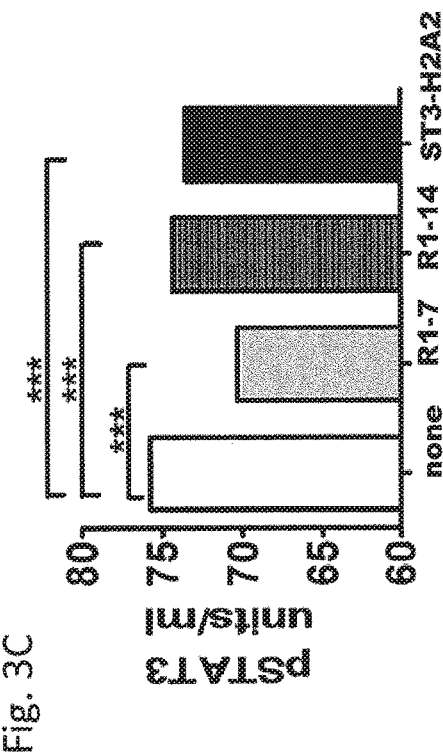
FIGS. 3A-3D are tables illustrating the effect of local pulmonary HDT with the peptide inhibitors IL10R1-7, IL10R1-14, and ST3-H2A2 on the stat3 and Il-10 transcripts and protein.
Figure 3B:
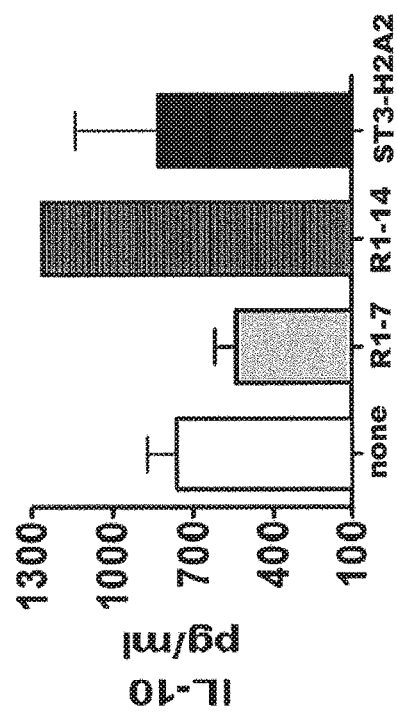

This example demonstrates the effect of the pulmonary treatment of the peptide inhibitors on stat3 and Il-40 transcripts and protein.

qRT-PCR was used to determine the effect of local pulmonary host directed therapy (HDT) using ST3-H2A2, IL10R1-7, and IL10R1-14 on the expression of stat3 and Il-10 transcripts in the lungs of mice infected for 60 days. The results represent the fold increase in stat3 and Il-10 RNA transcripts in the lungs of mice infected for 60 days compared to the expression for the same transcripts in similar samples obtained from naïve (unchallenged) mice (FIGS. 3A and 3B). In agreement with data shown in FIGS. 1A and 1B, the expression of transcripts for stat3 and Il-10 was upregulated in the lungs of mice with 60 days of Mtb infection and when compared to similar lung samples from age-matched naïve mice. The data has also shown no significant changes in the levels of pulmonary expression of stat3 after treatment with ST3-H2A2. However, samples from the same mice had increased levels of expression for the il-10 transcripts.

Figure 3C:
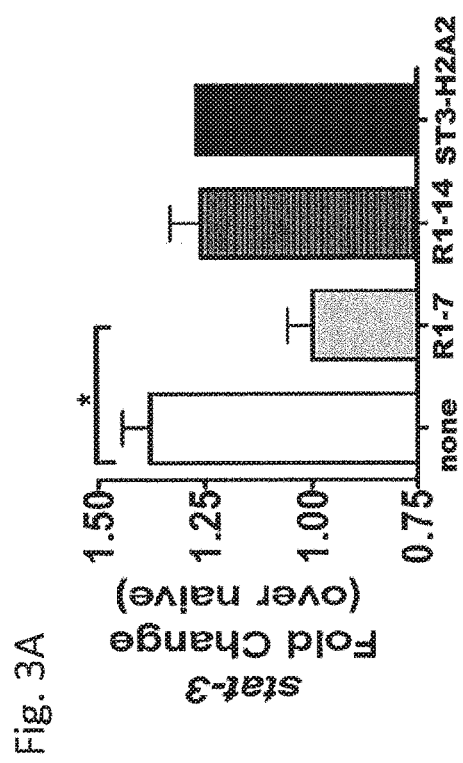
Figure 3D:
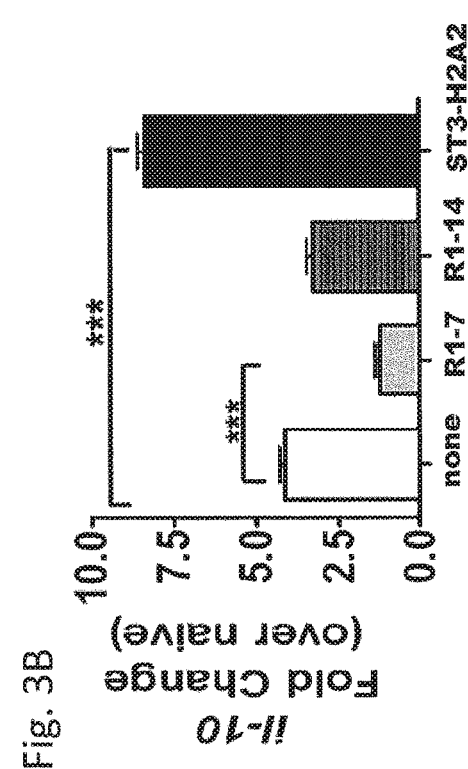

The levels of pSTAT3 and IL-10 in the lung homogenates obtained from the same mice were analyzed via ELISA and CBA, respectively (FIGS. 3C and 3D). ELISA revealed little change in the levels of pSTAT3 or IL-10 expression in lung samples after two weeks of treatment with ST3-H2A2 when compared to untreated control samples of mice chronically infected with Mtb. On the other hand, all samples from mice treated with IL10R1-7 presented lower levels of pSTAT3, STAT3, and IL-10 than those from control mice when analyzed by either RT-PCR or ELISA. Samples from mice receiving similar treatment with the IL10R1-14 peptide inhibitors showed no significant changes in the expression of pSTAT3, STAT3, and IL-10 when compared to control mice.

Example 5

This example demonstrates the effect on the expression of antimicrobial effector molecules after local intrapulmonary aerosol HDT with peptide inhibitors of STAT3 and IL-10.

The bactericidal capacity of the lungs against Mtb is dependent on enzymes such as nitric oxide synthase (NOS2) and phagocyte oxidase (phox also known as NADPH), which activities are the major sources of antimicrobial reactive nitrogen and oxygen intermediaries respectively known to effectively kill Mtb (Cunningham-Bussel et al., Proc. Natl. Acad. Sci. USA, 110: E4256-4265 (2013); MacMicking et al., Proc. Natl. Acad. Sci. USA, 94: 5243-5248 (1997); and Schnappinger et al., J. Exp. Med., 198: 693-704 (2003)). The NO (end product of NOS-2 activity) by itself or after reacting with .O radical (end product of NADPH oxidase metabolism) will generate .NOO radical with also very potent bactericidal activity against Mtb (Nicholson et al., Shock, 11: 253-258 (1999)). However, NOS2 activity is inhibited by high activity of the enzyme arginase 1 (Arg1) because NOS2 and Arg1 compete for the same substrate, L-arginine (Murray et al., Proc. Natl. Acad. Sci. USA, 102: 8686-8691 (2005)). Lysozyme produced by macrophages is another enzyme with potent antibacterial effect (Akinbi et al., J. Immunol., 165: 5760-5766 (2000); and Rosu et al., Microbiol. Res., 168: 153-164 (2013)).

Figure 4A:
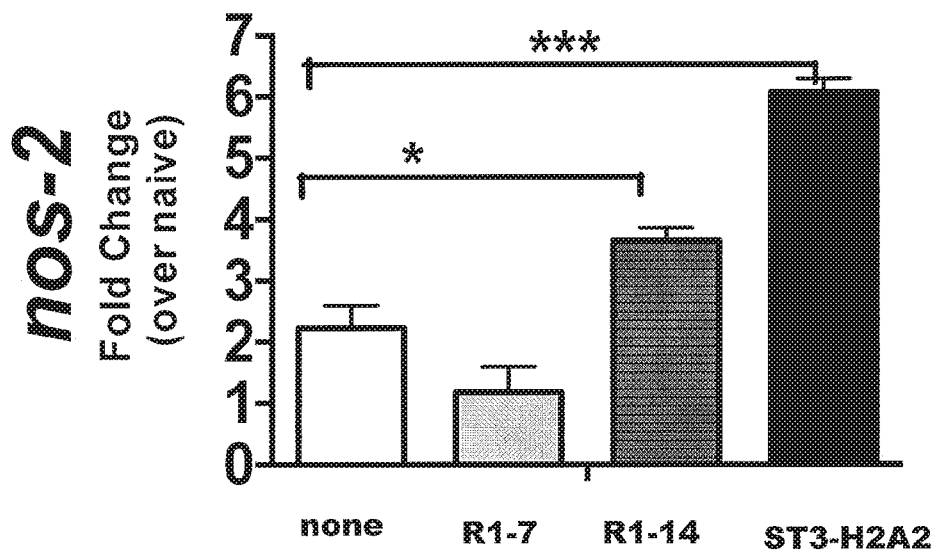
FIGS. 4A-4F are tables illustrating the effect on the expression of antimicrobial effector molecules after local intrapulmonary aerosol HDT with the peptide inhibitors IL10R1-7, IL10R1-14, and ST3-H2A2.
Figure 4B:
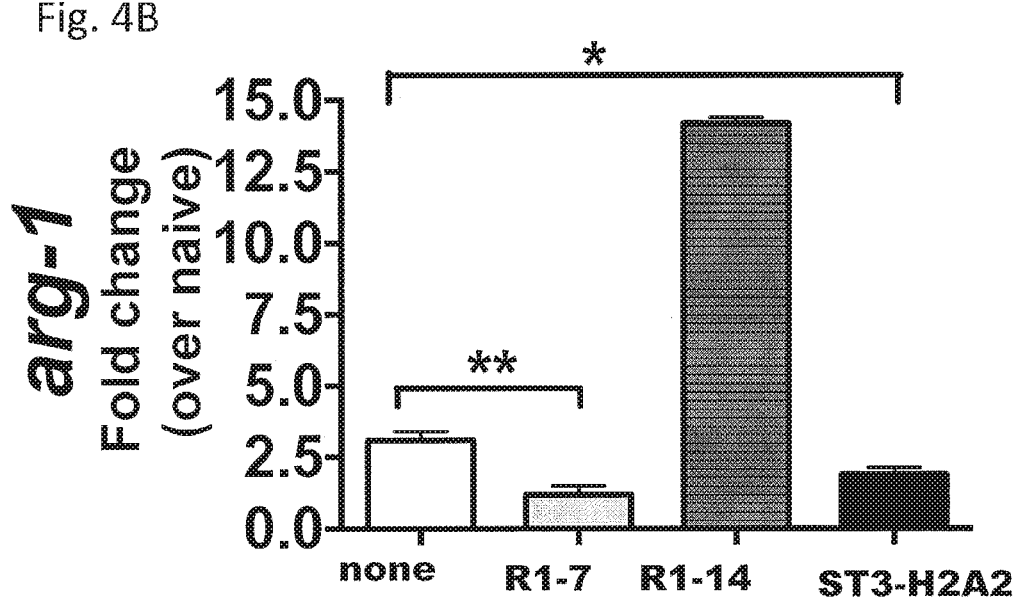
Figure 4C:
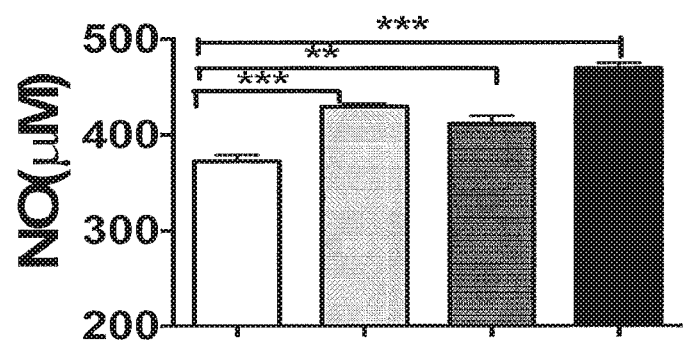
Figure 4D:
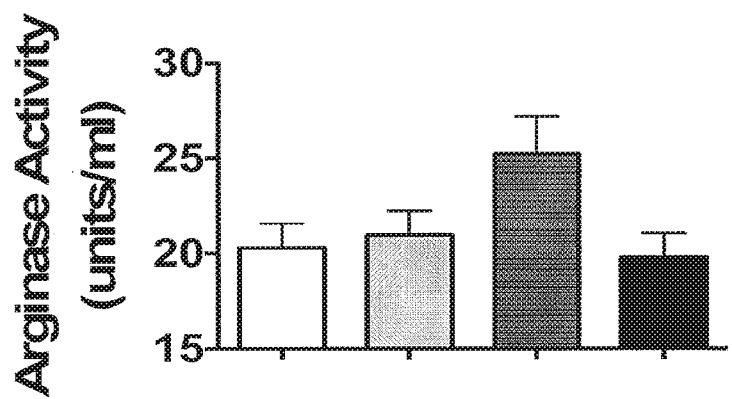
Figure 4E:
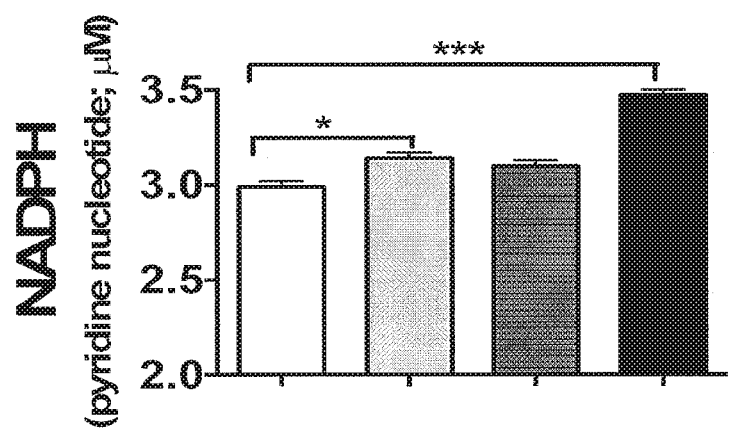
Figure 4F:
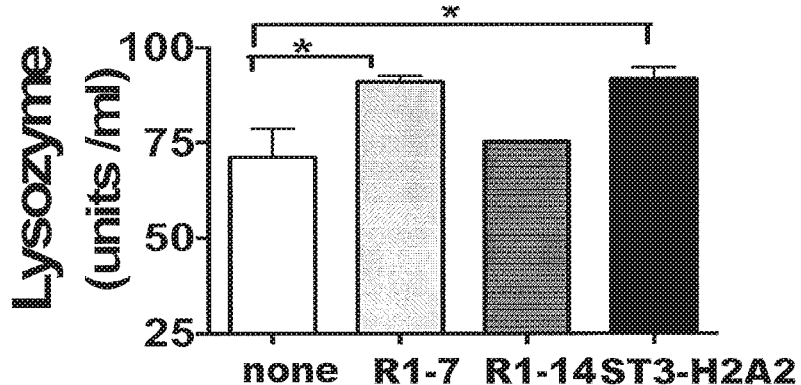
Figure 5A:
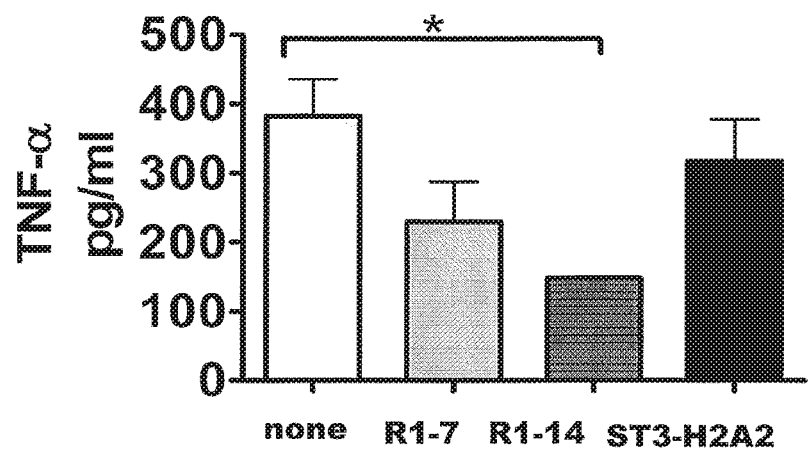
FIGS. 5A-5E are tables illustrating changes in the profile of Th1 cytokines after local intrapulmonary aerosol HDT with the peptide inhibitors IL10R1-7, IL10R1-14, and ST3-H2A2. CBA analyzing IL-6 (E), IL-12p40 (C), TNF-α (A), IFN-γ (B), and MCP-1 (D) was used to determine if local intrapulmonary aerosol HDT with the peptide inhibitors resulted in changes on the levels of inflammatory cytokines/chemokines. The concentration of each analyte was determined by extrapolating the mean fluorescence intensity (MFI) for each sample into the standard curves for every cytokine. Data is expressed as pg/ml of the sample. Data represent mean±SD of triplicates where * denotes p<0.05;  denotes p<0.01; and * denotes p<0.001 by Student's t test.
Figure 5B:
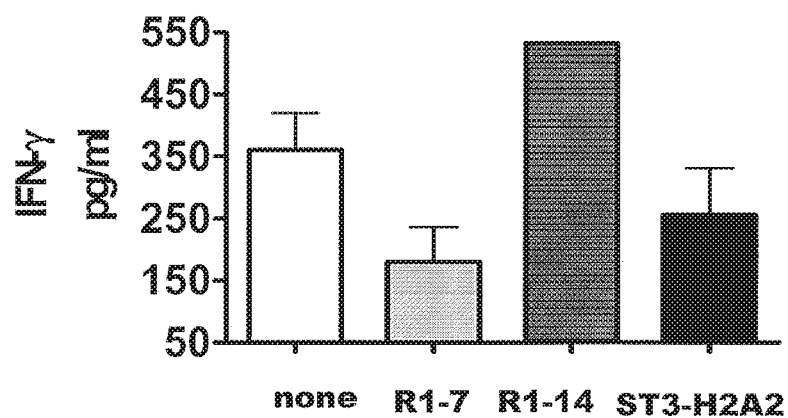
Figure 5C:
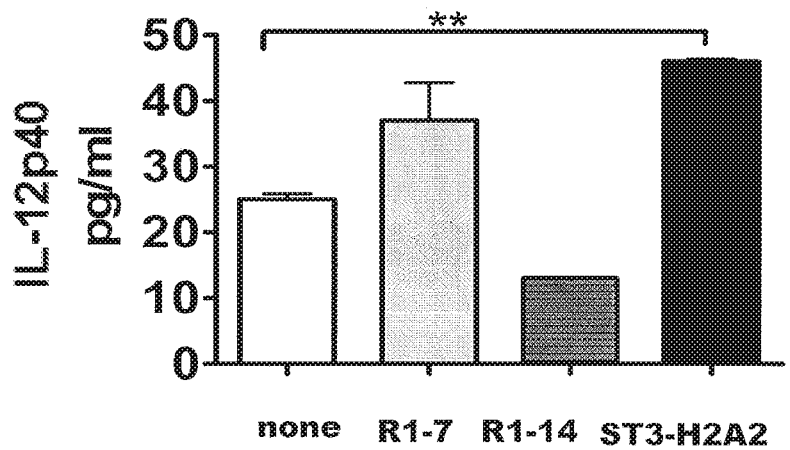
Figure 5D:
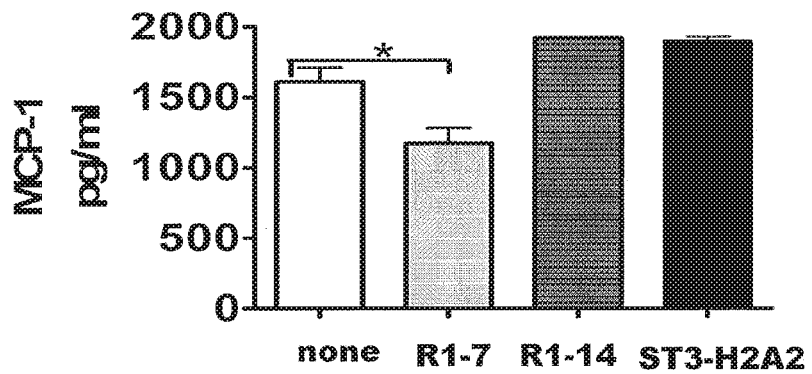
Figure 5E:
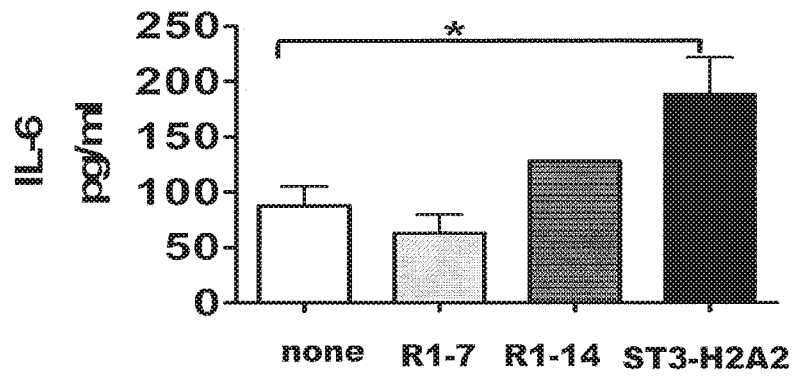
Figure 6A:
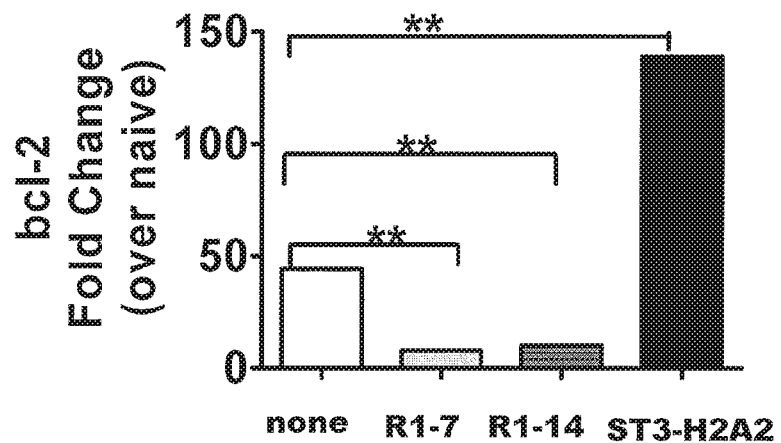
FIGS. 6A-6F are tables illustrating changes of important checkpoints in the apoptosis and autophagy pathways after local HDT with the peptide inhibitors IL10R1-7, IL10R1-14, and ST3-H2A2.
Figure 6B:
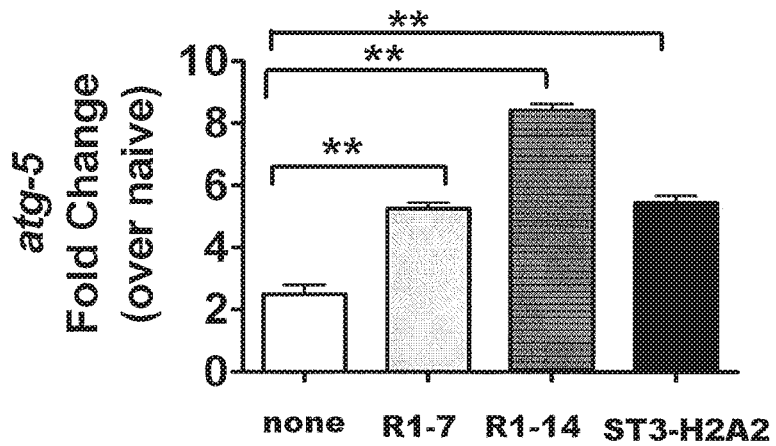
Figure 6C:
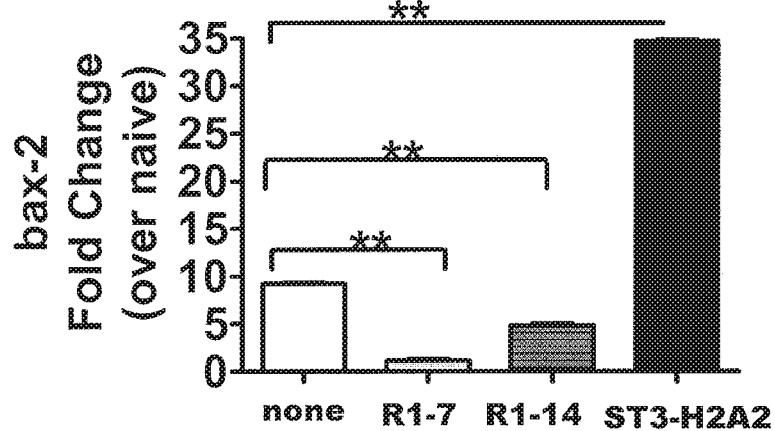
Figure 6D:
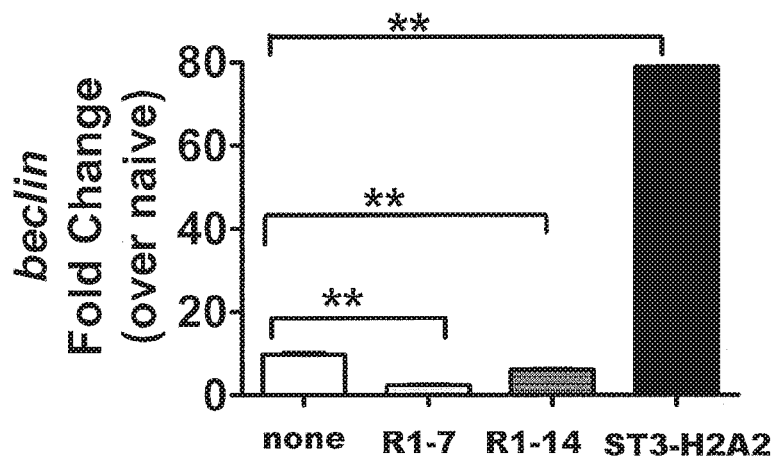
Figure 6E:
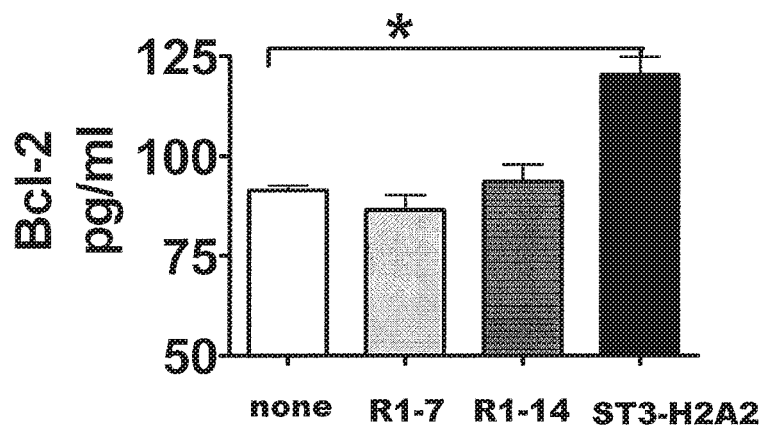
Figure 6F:
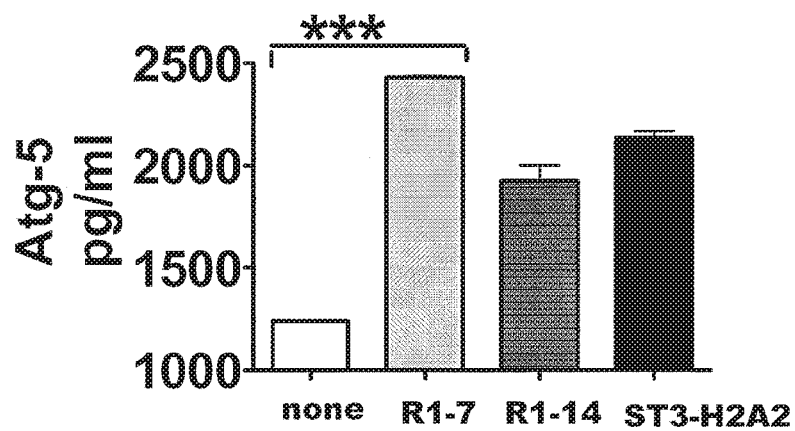

Thus, the outcome of the pulmonary aerosol HDT with peptide inhibitors was monitored by analyzing the content of NOS2 and Arg1 via RT-PCR as well as the enzymatic activity of NOS2, Arg1, NADPH and lysozyme using lung homogenates obtained from each mouse (FIGS. 4A and 4B). The mRNA nos2 expression increased more significantly in lung samples obtained from mice treated with the peptide inhibitor ST3-H2A2 when compared to similar samples obtained from control untreated mice chronically infected with Mtb. These changes correlated with decreased expression of mRNA transcript for arg1 in the same samples. Samples from mice treated with the IL10R1-14 also demonstrated a 2- to 10-fold increase in the nos2 and arg1 transcript expression respectively when compared to control mice. Samples obtained from the group of mice treated with IL10R1-7 showed reduction in transcript expression for nos2 and arg1 but not significantly for nos2.

The enzymatic activity of NOS, Arg1, NADPH, and lysozyme also were evaluated using lung homogenates and commercial kits. The activity for each of these enzymes was inferred by measuring concentrations of NO (NOS2), DQ substrate (lysozyme), and pyridine nucleotide (NADPH) in lung samples. These three metabolites were significantly elevated in mice treated with ST3-H2A2 or IL10R1-7 whereas as the activity of Arg1 was reduced or not changed when compared to similar samples obtained from control untreated mice chronically infected with Mtb (FIGS. 4A-4F). Similar samples obtained from IL10R1-14 showed lower or no increase for NOS2, NADPH, and lysozyme activity but had increased Arg1 activity when compared to control mice (FIGS. 4A-4F).

Example 6

This example demonstrates the changes in the profile of Th1 cytokines after local intrapulmonary aerosol HDT with peptide inhibitors of STAT3 and IL-10.

Effective immune response against TB is dependent on the development of a Th1 type immune response. The Th1 responses are characterized by expression of key cytokines such as TNFα, IL-12, and IFNγ among others. Cytometric bead assays to measure these cytokines revealed that local intrapulmonary aerosol HDT with ST3-H2A2, IL10R1-7, and IL10R1-14 had significant impact (see FIGS. 5A-5E). The levels of TNFα were reduced after treatment with all three peptides. Surprisingly, the levels of IFNγ expression in the lungs of mice treated with local HDT of peptide inhibitors ST3-H2A2 and IL10R1-7 also were decreased when compared to control mice, while the levels of expression of IFNγ in the lungs of IL10R1-14 treated mice were increased. Interestingly, the expression levels for the cytokines IL-12p40 and IL-6 were increased in the lungs of mice treated with local HDT with ST3-H2A2, but decreased in similar samples obtained from the IL10R1-7 treated mice and when compared to control mice.

Comparison of IFNγ expression with IL-12p40 expression between groups showed that they are almost reversed depending on the peptide inhibitor used. For IL10R1-7, IFNγ is down but IL-12p40 is up. For IL10R1-14, IFNγ is up but IL-12p40 is down. For ST3-H2A2, IFNγ is down but IL-12p40 is up. Also, the patterns of expression for both TNFα and IL-12p40 are similar with the exception of IL10R1-7 for which TNFα is down, but IL-12p40 is up when compared to controls.

Example 6

This example demonstrates the effect of local HDT with peptide inhibitors of STAT3 and IL-10 on lung histology.

The outcome of the pulmonary administration of HDT via aerosol of peptide inhibitors was analyzed at the histological level. Lung tissue sections from each group of mice were stained by H&E. All the groups presented granuloma lesions in the lungs. Accumulations of macrophages, many foamy cells, and clusters of lymphocytes formed the granulomas. The most noticeable observation when comparing the histopathology between H&E stained lungs sections from all groups of mice was increased numbers of clusters and highly packed lymphocytes in lung tissue sections obtained from groups of mice treated with either ST3-H2A2 or the IL10R1-7 and when compared to tissue sections obtained from Mtb infected mice without or IL10R1-14 treated mice.

Tissue sections from all groups of mice either not receiving treatment or treated with ST3-H2A2 or IL10R1-7 also were stained by IHC for pSTAT3. An interesting observation was reduced levels of pSTAT3 staining in the center of the granuloma lesions in tissue sections obtained from ST3-H2A2 or IL10R1-7-treated mice when compared to lung tissue sections obtained from Mtb with no treatment.

Example 7

This example demonstrates changes of important checkpoints in the apoptosis and autophagy pathways after local HDT with peptide inhibitors of STAT3 and IL-10.

STAT3 signaling has been described as an important pathway in the regulation of cell autophagy and apoptosis (Deng et al., *Cell Cycle*, 11: 367-376 (2012); and Jonchere et al. *Jak-Stat*, 2: e24353 (2013). Among the downstream effects resulting from persistent activation of the STAT3 is the activation of key proteins regulating the crosstalk between apoptosis and autophagy such as Bcl-2 (Jonchere et al., supra). Bcl-2 regulates apoptosis and autophagy by binding to Bax and Beclin-1, respectively. Moreover, Atg-5 is another key protein in autophagy described to be essential in the capacity of host macrophages to clear Mtb (Castillo et al., *Proc. Natl. Acad. Sci. USA*, 110: E4256-4265 (2012)).

To determine if localized HDT via administration of peptide inhibitors targeting the IL-10-STAT3 pathway would be able to modulate the expression of important checkpoints in the apoptotic and autophagy pathways, RT-PCR and ELISA were used to analyze transcripts or lung homogenate samples, respectively, obtained from each of the mice. qRT-PCR showed more that 3 fold increase in expression of bcl-2, bax, atg5 and beclin-1 in the samples obtained from mice receiving ST3-H2A2, whereas samples obtained from the IL10R1-7 and IL10R1-14-treated mice had increased expression of atg5 transcript only but had reduced expression of the bcl-2, bax and beclin-1 transcripts (FIGS. 6A-6F). When lung homogenates from each mouse were used to determine the levels of expression of Bcl-2 and Atg-5 protein using ELISA, the results were similar to those obtained by qRT-PCR.

Thus, Bcl-2 was significantly increased only in samples from ST3-H2A2-treated mice when compared to samples from control untreated mice with a chronic infection with Mtb. Atg-5 was increased in samples obtained from mice treated with all three peptide inhibitors when compared to control mice.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating an infection of *Mycobacteriaceae* sp. in an animal in need thereof, comprising administering a therapeutically effective amount of a peptide-based inhibitor of STAT3 or a nucleic acid encoding the peptide-based inhibitor to the animal, wherein the peptide-based inhibitor comprises the amino acid sequence of any one of SEQ ID NOs: 40, 42, 44, 46, 48, 49, 55-57, 66-76, or the inverse sequence thereof, wherein:

SEQ ID NO: 40 is $x^1$TRYL$x^3$QLHKLY (SEQ ID NO: 40),

SEQ ID NO: 42 is $x^1$TRYL$x^3$QLHKLY$x^6$ (SEQ ID NO: 42),

SEQ ID NO: 44 is YLKHLQ$x^3$LYRT$x^1$ (SEQ ID NO: 44),

SEQ ID NO: 46 is $x^6$YLKHLQ$x^3$LYRT$x^1$ (SEQ ID NO: 46), wherein $x^1$ is D, A, or N, $x^3$ is E or Q, and $x^6$ is K, R, or S, thereby treating the infection in the animal.

2. The method of claim 1, wherein the *Mycobacteriaceae* sp. is *Mycobacterium tuberculosis*.

3. The method of claim 1, wherein the peptide-based inhibitor comprises the amino acid sequence of SEQ ID NO: 65 (ST3-H2A2).

4. The method of claim 1, wherein administering the peptide-based inhibitor to the animal results in reduced *Mycobacterium tuberculosis* (Mtb) bacilli load in the lungs of the animal.

5. The method of claim 1, wherein the animal is undergoing sequential or simultaneous tuberculosis therapy.

6. The method of claim 5, wherein the tuberculosis therapy is antibiotic treatment.

7. The method of claim 1, wherein the animal is selected from the group consisting of mice, rats, horses, cows, sheep, dogs, cats, and primates.

8. The method of claim 7, wherein the animal is a human.

9. The method of claim 1, wherein the peptide-based inhibitor comprises D-amino acids.

10. The method of claim 1, wherein the peptide-based inhibitor further comprises a cell-penetrating motif.

11. The method of claim 10, wherein the cell-penetrating motif is a protein transduction domain or fatty acid, optionally attached to the peptide-based inhibitor via a linker sequence.

12. The method of claim 1, wherein the peptide-based inhibitor comprises a terminal acetyl or palmitoyl group.

13. The method of claim 12, wherein the peptide-based inhibitor comprises a terminal ε-palmitoyl modified lysine residue.

14. The method of claim 1, wherein the nucleic acid is in the form of a vector.

15. The method of claim 1, wherein the peptide-based inhibitor is administered in the form of a pharmaceutical composition.

16. The method of claim 1, wherein the peptide-based inhibitor is administered as an inhalant.

17. A method of treating a disease selected from tuberculosis, Wegener's granulomatosis, and chronic granulomatous disease in an animal in need thereof, comprising administering a therapeutically effective amount of a peptide-based inhibitor of STAT3 or a nucleic acid encoding the peptide-based inhibitor to the animal, wherein the peptide-based inhibitor comprises the amino acid sequence of any one of SEQ ID NOs: 40, 42, 44, 46, 48, 49, 55-57, 66-76, or the inverse sequence thereof, wherein:

SEQ ID NO: 40 is $x^1$TRYL$x^3$QLHKLY (SEQ ID NO: 40),

SEQ ID NO: 42 is $x^1$TRYL$x^3$QLHKLY$x^6$ (SEQ ID NO: 42),

SEQ ID NO: 44 is YLKHLQ$x^3$LYRT$x^1$ (SEQ ID NO: 44),

SEQ ID NO: 46 is $x^6$YLKHLQ$x^3$LYRT$x^1$ (SEQ ID NO: 46), wherein $x^1$ is D, A, or N, $x^3$ is E or Q, and $x^6$ is K, R, or S, thereby treating the disease in the animal.

18. The method of claim 17, wherein the disease is tuberculosis.

19. The method of claim 17, wherein the disease is Wegener's granulomatosis.

20. The method of claim 17, wherein the disease is chronic granulomatous disease.

\* \* \* \* \*

SEQUENCE LISTING

```
<160> NUMBER OF SEQ ID NOS: 90

<210> SEQ ID NO 1
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: wherein x can be any amino acid
<220> FEATURE:
<221> NAME/KEY: MISC_FEATURE
<222> LOCATION: (4)..(4)
<223> OTHER INFORMATION: wherein x can be any amino acid
<220> FEATURE:
<221> NAME/KEY: MISC_FEATURE
<222> LOCATION: (6)..(6)
<223> OTHER INFORMATION: wherein x can be any amino acid

<400> SEQUENCE: 1

Xaa Val Leu Xaa Phe Xaa Lys
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Ser Val Leu Leu Phe Lys Lys
1               5

<210> SEQ ID NO 3
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Leu modified with palmitoyl group
<220> FEATURE:
<221> NAME/KEY: MISC_FEATURE
<222> LOCATION: (17)..(17)
<223> OTHER INFORMATION: Lys modified with an amino group

<400> SEQUENCE: 3

Xaa Tyr Val Arg Arg Arg Lys Lys Leu Pro Ser Val Leu Leu Phe Lys
1               5                   10                  15

Xaa

<210> SEQ ID NO 4
<211> LENGTH: 13
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Epsilon-palmitoyl modified lysine
<220> FEATURE:
<221> NAME/KEY: MISC_FEATURE
<222> LOCATION: (13)..(13)
<223> OTHER INFORMATION: Ser modified with amino group

<400> SEQUENCE: 4

Xaa Lys Leu Pro Ser Val Leu Leu Phe Lys Lys Pro Xaa
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: All the amino acids are D-amino acids
<220> FEATURE:
<221> NAME/KEY: MISC_FEATURE
<222> LOCATION: (1)..(1)
<223> OTHER INFORMATION: Ser modified with acetyl group
<220> FEATURE:
<221> NAME/KEY: MISC_FEATURE
<222> LOCATION: (13)..(13)
<223> OTHER INFORMATION: Epsilon-palmitoyl modified lysine

<400> SEQUENCE: 5

Xaa Pro Lys Lys Phe Leu Leu Val Ser Pro Leu Lys Xaa
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: All the amino acids are D-amino acids
<220> FEATURE:
<221> NAME/KEY: MISC_FEATURE
<222> LOCATION: (1)..(1)
<223> OTHER INFORMATION: Lys modified with acetyl group
<220> FEATURE:
<221> NAME/KEY: MISC_FEATURE
<222> LOCATION: (11)..(11)
<223> OTHER INFORMATION: Epsilon-palmitoyl modified lysine

<400> SEQUENCE: 6

Xaa Lys Phe Leu Leu Val Ser Pro Leu Lys Xaa
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: All the amino acids are D-amino acids
<220> FEATURE:
<221> NAME/KEY: MISC_FEATURE
<222> LOCATION: (1)..(1)
```

```
<223> OTHER INFORMATION: Pro modified with acetyl group
<220> FEATURE:
<221> NAME/KEY: MISC_FEATURE
<222> LOCATION: (12)..(12)
<223> OTHER INFORMATION: Epsilon-palmitoyl modified lysine

<400> SEQUENCE: 7

Xaa Lys Lys Phe Leu Leu Val Ser Pro Leu Lys Xaa
1               5                   10

<210> SEQ ID NO 8
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: wherein x can be any amino acid
<220> FEATURE:
<221> NAME/KEY: MISC_FEATURE
<222> LOCATION: (12)..(12)
<223> OTHER INFORMATION: wherein x can be any amino acid
<220> FEATURE:
<221> NAME/KEY: MISC_FEATURE
<222> LOCATION: (18)..(18)
<223> OTHER INFORMATION: wherein x can be any amino acid

<400> SEQUENCE: 8

Leu His Gly Ser Thr Xaa Ser Gly Phe Gly Ser Xaa Lys Pro Ser Leu
1               5                   10                  15

Gln Xaa

<210> SEQ ID NO 9
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: wherein x is Asp or Asn

<400> SEQUENCE: 9

Leu His Gly Ser Thr Xaa Ser Gly Phe Gly Ser Thr Lys Pro Ser Leu
1               5                   10                  15

Gln Thr

<210> SEQ ID NO 10
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Leu modified with palmitoyl group

<400> SEQUENCE: 10

Xaa His Gly Ser Thr Asp Ser Gly Phe Gly Ser Thr Lys Pro Ser Leu
1               5                   10                  15

Gln Thr

<210> SEQ ID NO 11
<211> LENGTH: 21
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: All the amino acids are D-amino acids
<220> FEATURE:
<221> NAME/KEY: MISC_FEATURE
<222> LOCATION: (1)..(1)
<223> OTHER INFORMATION: Glu modified with acetyl group
<220> FEATURE:
<221> NAME/KEY: MISC_FEATURE
<222> LOCATION: (21)..(21)
<223> OTHER INFORMATION: Epsilon-palmitoyl modified lysine

<400> SEQUENCE: 11

Xaa Glu Thr Gln Leu Ser Pro Lys Thr Ser Gly Phe Gly Ser Asp Thr
1               5                   10                  15

Ser Gly His Leu Xaa
            20

<210> SEQ ID NO 12
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: All the amino acids are D-amino acids
<220> FEATURE:
<221> NAME/KEY: MISC_FEATURE
<222> LOCATION: (1)..(1)
<223> OTHER INFORMATION: Glu modified with acetyl group
<220> FEATURE:
<221> NAME/KEY: MISC_FEATURE
<222> LOCATION: (20)..(20)
<223> OTHER INFORMATION: Epsilon-palmitoyl modified lysine

<400> SEQUENCE: 12

Xaa Thr Gln Leu Ser Pro Lys Thr Ser Gly Phe Gly Ser Asp Thr Ser
1               5                   10                  15

Gly His Leu Xaa
            20

<210> SEQ ID NO 13
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: All the amino acids are D-amino acids
<220> FEATURE:
<221> NAME/KEY: MISC_FEATURE
<222> LOCATION: (1)..(1)
<223> OTHER INFORMATION: Thr modified with acetyl group
<220> FEATURE:
<221> NAME/KEY: MISC_FEATURE
<222> LOCATION: (19)..(19)
<223> OTHER INFORMATION: Epsilon-palmitoyl modified lysine

<400> SEQUENCE: 13

Xaa Gln Leu Ser Pro Lys Thr Ser Gly Phe Gly Ser Asp Thr Ser Gly
1               5                   10                  15

His Leu Xaa

<210> SEQ ID NO 14
```

<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: All the amino acids are D-amino acids
<220> FEATURE:
<221> NAME/KEY: MISC_FEATURE
<222> LOCATION: (1)..(1)
<223> OTHER INFORMATION: Epsilon-palmitoyl modified lysine
<220> FEATURE:
<221> NAME/KEY: MISC_FEATURE
<222> LOCATION: (19)..(19)
<223> OTHER INFORMATION: Leu modified with amino group

<400> SEQUENCE: 14

Xaa Thr Gln Leu Ser Pro Lys Thr Ser Gly Phe Gly Ser Asp Thr Ser
1               5                   10                  15

Gly His Xaa

<210> SEQ ID NO 15
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: All the amino acids are D-amino acids
<220> FEATURE:
<221> NAME/KEY: MISC_FEATURE
<222> LOCATION: (1)..(1)
<223> OTHER INFORMATION: Epsilon-palmitoyl modified lysine
<220> FEATURE:
<221> NAME/KEY: MISC_FEATURE
<222> LOCATION: (21)..(21)
<223> OTHER INFORMATION: Leu modified with amino group

<400> SEQUENCE: 15

Xaa Glu Glu Thr Gln Leu Ser Pro Lys Thr Ser Gly Phe Gly Ser Asp
1               5                   10                  15

Thr Ser Gly His Xaa
            20

<210> SEQ ID NO 16
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: All the amino acids are D-amino acids
<220> FEATURE:
<221> NAME/KEY: MISC_FEATURE
<222> LOCATION: (1)..(1)
<223> OTHER INFORMATION: Epsilon-palmitoyl modified lysine
<220> FEATURE:
<221> NAME/KEY: MISC_FEATURE
<222> LOCATION: (19)..(19)
<223> OTHER INFORMATION: Leu modified with amino group

<400> SEQUENCE: 16

Xaa Thr Gln Leu Ser Pro Lys Thr Ser Gly Phe Gly Ser Asn Thr Ser
1               5                   10                  15

Gly His Xaa

<210> SEQ ID NO 17

```
<211> LENGTH: 8
<212> TYPE: PRT
<213> ORGANISM: Artificial Sequence
<220> FEATURE:
<223> OTHER INFORMATION: Synthetic

<400> SEQUENCE: 17

Thr Asp Ser Gly Ile Cys Leu Gln
1               5

<210> SEQ ID NO 18
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Cyclic peptide with a disulfide bond bridging
      the Cys residues
<220> FEATURE:
<221> NAME/KEY: MISC_FEATURE
<222> LOCATION: (1)..(1)
<223> OTHER INFORMATION: Epsilon-palmitoyl modified lysine

<400> SEQUENCE: 18

Xaa Thr Cys Gly Asp Asn Thr Asp Ser Gly Ile Cys Leu Gln
1               5                   10

<210> SEQ ID NO 19
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Cyclic peptide with a disulfide bond bridging
      the Cys residues
<220> FEATURE:
<221> NAME/KEY: MISC_FEATURE
<222> LOCATION: (1)..(1)
<223> OTHER INFORMATION: Epsilon-palmitoyl modified lysine

<400> SEQUENCE: 19

Xaa Ser Cys Ser Ser Gly Ser Ser Asn Ser Thr Asp Ser Gly Ile Cys
1               5                   10                  15

Leu Gln

<210> SEQ ID NO 20
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: wherein x can be any amino acid
<220> FEATURE:
<221> NAME/KEY: MISC_FEATURE
<222> LOCATION: (5)..(5)
<223> OTHER INFORMATION: wherein x can be any amino acid
<220> FEATURE:
<221> NAME/KEY: MISC_FEATURE
<222> LOCATION: (6)..(6)
<223> OTHER INFORMATION: wherein x can be any amino acid

<400> SEQUENCE: 20

Phe Xaa Gly Tyr Xaa Xaa Gln Thr Arg
1               5
```

```
<210> SEQ ID NO 21
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: wherein x can be any amino acid
<220> FEATURE:
<221> NAME/KEY: MISC_FEATURE
<222> LOCATION: (12)..(12)
<223> OTHER INFORMATION: wherein x can be any amino acid

<400> SEQUENCE: 21

Leu His Gly Ser Thr Xaa Ser Gly Phe Gly Ser Xaa Lys
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Epsilon-palmitoyl modified lysine
<220> FEATURE:
<221> NAME/KEY: MISC_FEATURE
<222> LOCATION: (10)..(10)
<223> OTHER INFORMATION: Arg modified with amino group

<400> SEQUENCE: 22

Xaa Phe Gln Gly Tyr Leu Arg Gln Thr Xaa
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Ala modified with palmitoyl group
<220> FEATURE:
<221> NAME/KEY: MISC_FEATURE
<222> LOCATION: (10)..(10)
<223> OTHER INFORMATION: Arg modified with amino group

<400> SEQUENCE: 23

Xaa Phe Gln Gly Tyr Leu Arg Gln Thr Xaa
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: All the amino acids are D-amino acids
<220> FEATURE:
<221> NAME/KEY: MISC_FEATURE
<222> LOCATION: (1)..(1)
<223> OTHER INFORMATION: Arg modified with acetyl group
<220> FEATURE:
```

-continued

```
<221> NAME/KEY: MISC_FEATURE
<222> LOCATION: (10)..(10)
<223> OTHER INFORMATION: Epsilon-palmitoyl modified lysine

<400> SEQUENCE: 24

Xaa Thr Gln Arg Leu Tyr Gly Gln Phe Xaa
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: wherein x can be any amino acid

<400> SEQUENCE: 25

Ala Xaa Gly Tyr Leu Lys Gln
1               5

<210> SEQ ID NO 26
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Epsilon-palmitoyl modified lysine
<220> FEATURE:
<221> NAME/KEY: MISC_FEATURE
<222> LOCATION: (12)..(12)
<223> OTHER INFORMATION: Gln modified with amino group

<400> SEQUENCE: 26

Xaa Pro Pro Ala Leu Ala Lys Gly Tyr Leu Lys Xaa
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Epsilon-palmitoyl modified lysine
<220> FEATURE:
<221> NAME/KEY: MISC_FEATURE
<222> LOCATION: (13)..(13)
<223> OTHER INFORMATION: Glu modified with amino group

<400> SEQUENCE: 27

Xaa Pro Pro Ala Leu Ala Lys Gly Tyr Leu Lys Gln Xaa
1               5                   10

<210> SEQ ID NO 28
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Epsilon-palmitoyl modified lysine
```

```
<220> FEATURE:
<221> NAME/KEY: MISC_FEATURE
<222> LOCATION: (8)..(8)
<223> OTHER INFORMATION: Gln modified with amino group

<400> SEQUENCE: 28

Xaa Ala Lys Gly Tyr Leu Lys Xaa
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Leu modified with palmitoyl group
<220> FEATURE:
<221> NAME/KEY: MISC_FEATURE
<222> LOCATION: (8)..(8)
<223> OTHER INFORMATION: Gln modified with amino group

<400> SEQUENCE: 29

Xaa Ala Lys Gly Tyr Leu Lys Xaa
1               5

<210> SEQ ID NO 30
<211> LENGTH: 10
<212> TYPE: PRT
<213> ORGANISM: Artificial Sequence
<220> FEATURE:
<223> OTHER INFORMATION: Synthetic

<400> SEQUENCE: 30

Leu Val Thr Leu Pro Leu Ile Ser Ser Leu
1               5                   10

<210> SEQ ID NO 31
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Epsilon-palmitoyl modified lysine
<220> FEATURE:
<221> NAME/KEY: MISC_FEATURE
<222> LOCATION: (15)..(15)
<223> OTHER INFORMATION: Glu modified with amino group

<400> SEQUENCE: 31

Xaa Leu Val Thr Leu Pro Leu Ile Ser Ser Leu Gln Ser Ser Xaa
1               5                   10                  15

<210> SEQ ID NO 32
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Epsilon-palmitoyl modified lysine
<220> FEATURE:
<221> NAME/KEY: MISC_FEATURE
<222> LOCATION: (12)..(12)
```

<223> OTHER INFORMATION: Gln modified with amino group

<400> SEQUENCE: 32

Xaa Leu Val Thr Leu Pro Leu Ile Ser Ser Leu Xaa
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Epsilon-palmitoyl modified lysine
<220> FEATURE:
<221> NAME/KEY: MISC_FEATURE
<222> LOCATION: (11)..(11)
<223> OTHER INFORMATION: Leu modified with amino group

<400> SEQUENCE: 33

Xaa Leu Val Thr Leu Pro Leu Ile Ser Ser Xaa
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Epsilon-palmitoyl modified lysine
<220> FEATURE:
<221> NAME/KEY: MISC_FEATURE
<222> LOCATION: (12)..(12)
<223> OTHER INFORMATION: Leu modified with amino group

<400> SEQUENCE: 34

Xaa Asn Leu Val Thr Leu Pro Leu Ile Ser Ser Xaa
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Leu modified with palmitoyl group

<400> SEQUENCE: 35

Xaa His Gly Ser Thr Asp Ser Gly Phe Gly Ser Thr Lys
1               5                   10

<210> SEQ ID NO 36
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: wherein x can be any amino acid
<220> FEATURE:
<221> NAME/KEY: MISC_FEATURE

```
<222> LOCATION: (7)..(7)
<223> OTHER INFORMATION: wherein x can be any amino acid

<400> SEQUENCE: 36

Pro Xaa His Leu Lys Glu Xaa Leu
1               5

<210> SEQ ID NO 37
<211> LENGTH: 13
<212> TYPE: PRT
<213> ORGANISM: Artificial Sequence
<220> FEATURE:
<223> OTHER INFORMATION: Synthetic

<400> SEQUENCE: 37

Ser Glu Phe Asp Ile Phe Ile Asn Tyr Ile Glu Ala Tyr
1               5                   10

<210> SEQ ID NO 38
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Tyr modified with Ac-C(Fluo)
<220> FEATURE:
<221> NAME/KEY: MISC_FEATURE
<222> LOCATION: (4)..(4)
<223> OTHER INFORMATION: wherein x is norleucine
<220> FEATURE:
<221> NAME/KEY: MISC_FEATURE
<222> LOCATION: (18)..(18)
<223> OTHER INFORMATION: wherein x is norleucine
<220> FEATURE:
<221> NAME/KEY: MISC_FEATURE
<222> LOCATION: (20)..(20)
<223> OTHER INFORMATION: wherein x is norleucine
<220> FEATURE:
<221> NAME/KEY: MISC_FEATURE
<222> LOCATION: (24)..(24)
<223> OTHER INFORMATION: Asn modified with amino group

<400> SEQUENCE: 38

Xaa Lys Ala Xaa Ser Glu Phe Asp Ile Phe Ile Asn Tyr Ile Glu Ala
1               5                   10                  15

Tyr Xaa Thr Xaa Lys Ile Arg Xaa
            20

<210> SEQ ID NO 39
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: wherein x can be any amino acid
<220> FEATURE:
<221> NAME/KEY: MISC_FEATURE
<222> LOCATION: (3)..(3)
<223> OTHER INFORMATION: wherein x can be any amino acid
<220> FEATURE:
<221> NAME/KEY: MISC_FEATURE
<222> LOCATION: (6)..(7)
<223> OTHER INFORMATION: wherein x can be any amino acid
<220> FEATURE:
<221> NAME/KEY: MISC_FEATURE
<222> LOCATION: (10)..(10)
```

<223> OTHER INFORMATION: wherein x can be any amino acid
<220> FEATURE:
<221> NAME/KEY: MISC_FEATURE
<222> LOCATION: (12)..(12)
<223> OTHER INFORMATION: wherein x can be any amino acid

<400> SEQUENCE: 39

Xaa Thr Xaa Tyr Leu Xaa Xaa Leu His Xaa Leu Xaa
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: wherein x can be any amino acid
<220> FEATURE:
<221> NAME/KEY: MISC_FEATURE
<222> LOCATION: (6)..(6)
<223> OTHER INFORMATION: wherein x can be any amino acid

<400> SEQUENCE: 40

Xaa Thr Arg Tyr Leu Xaa Gln Leu His Lys Leu Tyr
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: wherein x can be any amino acid
<220> FEATURE:
<221> NAME/KEY: MISC_FEATURE
<222> LOCATION: (3)..(3)
<223> OTHER INFORMATION: wherein x can be any amino acid
<220> FEATURE:
<221> NAME/KEY: MISC_FEATURE
<222> LOCATION: (6)..(7)
<223> OTHER INFORMATION: wherein x can be any amino acid
<220> FEATURE:
<221> NAME/KEY: MISC_FEATURE
<222> LOCATION: (10)..(10)
<223> OTHER INFORMATION: wherein x can be any amino acid
<220> FEATURE:
<221> NAME/KEY: MISC_FEATURE
<222> LOCATION: (12)..(13)
<223> OTHER INFORMATION: wherein x can be any amino acid

<400> SEQUENCE: 41

Xaa Thr Xaa Tyr Leu Xaa Xaa Leu His Xaa Leu Xaa Xaa
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: wherein x can be any amino acid
<220> FEATURE:
<221> NAME/KEY: MISC_FEATURE
<222> LOCATION: (6)..(6)

```
<223> OTHER INFORMATION: wherein x can be any amino acid
<220> FEATURE:
<221> NAME/KEY: MISC_FEATURE
<222> LOCATION: (13)..(13)
<223> OTHER INFORMATION: wherein x can be any amino acid

<400> SEQUENCE: 42

Xaa Thr Arg Tyr Leu Xaa Gln Leu His Lys Leu Tyr Xaa
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be any amino acid and may or may not be
      present
<220> FEATURE:
<221> NAME/KEY: MISC_FEATURE
<222> LOCATION: (2)..(2)
<223> OTHER INFORMATION: wherein x can be any amino acid
<220> FEATURE:
<221> NAME/KEY: MISC_FEATURE
<222> LOCATION: (4)..(4)
<223> OTHER INFORMATION: wherein x can be any amino acid
<220> FEATURE:
<221> NAME/KEY: MISC_FEATURE
<222> LOCATION: (7)..(8)
<223> OTHER INFORMATION: wherein x can be any amino acid
<220> FEATURE:
<221> NAME/KEY: MISC_FEATURE
<222> LOCATION: (11)..(11)
<223> OTHER INFORMATION: wherein x can be any amino acid
<220> FEATURE:
<221> NAME/KEY: MISC_FEATURE
<222> LOCATION: (13)..(13)
<223> OTHER INFORMATION: wherein x can be any amino acid

<400> SEQUENCE: 43

Xaa Xaa Leu Xaa His Leu Xaa Xaa Leu Tyr Xaa Thr Xaa
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be any amino acid and may or may not be
      present
<220> FEATURE:
<221> NAME/KEY: MISC_FEATURE
<222> LOCATION: (8)..(8)
<223> OTHER INFORMATION: wherein x can be any amino acid
<220> FEATURE:
<221> NAME/KEY: MISC_FEATURE
<222> LOCATION: (13)..(13)
<223> OTHER INFORMATION: wherein x can be any amino acid

<400> SEQUENCE: 44

Xaa Tyr Leu Lys His Leu Gln Xaa Leu Tyr Arg Thr Xaa
1               5                   10

<210> SEQ ID NO 45
<211> LENGTH: 13
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: wherein x can be any amino acid
<220> FEATURE:
<221> NAME/KEY: MISC_FEATURE
<222> LOCATION: (4)..(4)
<223> OTHER INFORMATION: wherein x can be any amino acid
<220> FEATURE:
<221> NAME/KEY: MISC_FEATURE
<222> LOCATION: (7)..(8)
<223> OTHER INFORMATION: wherein x can be any amino acid
<220> FEATURE:
<221> NAME/KEY: MISC_FEATURE
<222> LOCATION: (11)..(11)
<223> OTHER INFORMATION: wherein x can be any amino acid
<220> FEATURE:
<221> NAME/KEY: MISC_FEATURE
<222> LOCATION: (13)..(13)
<223> OTHER INFORMATION: wherein x can be any amino acid

<400> SEQUENCE: 45

Xaa Xaa Leu Xaa His Leu Xaa Xaa Leu Tyr Xaa Thr Xaa
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: wherein x can be any amino acid
<220> FEATURE:
<221> NAME/KEY: MISC_FEATURE
<222> LOCATION: (8)..(8)
<223> OTHER INFORMATION: wherein x can be any amino acid
<220> FEATURE:
<221> NAME/KEY: MISC_FEATURE
<222> LOCATION: (13)..(13)
<223> OTHER INFORMATION: wherein x can be any amino acid

<400> SEQUENCE: 46

Xaa Tyr Leu Lys His Leu Gln Xaa Leu Tyr Arg Thr Xaa
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Synthetic

<400> SEQUENCE: 47

Leu Asp Thr Arg Tyr Leu Glu Gln Leu His Gln Leu Tyr Ser
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Synthetic

<400> SEQUENCE: 48

Asp Thr Arg Tyr Leu Glu Gln Leu His Lys Leu Tyr Ser
1               5                   10
```

<210> SEQ ID NO 49
<211> LENGTH: 14
<212> TYPE: PRT
<213> ORGANISM: Artificial Sequence
<220> FEATURE:
<223> OTHER INFORMATION: Synthetic

<400> SEQUENCE: 49

Leu Asp Thr Arg Tyr Leu Glu Gln Leu His Lys Leu Tyr Ser
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: X is 4-cyano phenylalanine

<400> SEQUENCE: 50

Asp Thr Arg Tyr Leu Glu Gln Leu His Lys Leu Xaa Ser
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Synthetic

<400> SEQUENCE: 51

Asp Thr Lys Tyr Leu Glu Gln Leu His Lys Leu Tyr Ser
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Synthetic

<400> SEQUENCE: 52

Asp Thr Arg Tyr Leu Gln Glu Leu His Lys Leu Tyr Ser
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: X is Diaminobutyric acid

<400> SEQUENCE: 53

Asp Thr Arg Tyr Leu Glu Gln Leu His Xaa Leu Tyr Ser
1               5                   10

<210> SEQ ID NO 54
<211> LENGTH: 22
<212> TYPE: PRT
<213> ORGANISM: Artificial Sequence

```
<220> FEATURE:
<223> OTHER INFORMATION: Synthetic

<400> SEQUENCE: 54

Ala Gln Trp Asn Gln Leu Gln Gln Leu Asp Thr Arg Tyr Leu Glu Gln
1               5                   10                  15

Leu His Gln Leu Tyr Ser
            20

<210> SEQ ID NO 55
<211> LENGTH: 13
<212> TYPE: PRT
<213> ORGANISM: Artificial Sequence
<220> FEATURE:
<223> OTHER INFORMATION: Synthetic

<400> SEQUENCE: 55

Leu Asp Thr Arg Tyr Leu Glu Gln Leu His Lys Leu Tyr
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Synthetic

<400> SEQUENCE: 56

Asp Thr Arg Tyr Leu Glu Gln Leu His Lys Leu Tyr
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Asp modified with acetyl group

<400> SEQUENCE: 57

Xaa Thr Arg Tyr Leu Glu Gln Leu His Lys Leu Tyr
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: X is Diaminobutyric acid.

<400> SEQUENCE: 58

Leu Asp Thr Arg Tyr Leu Glu Gln Leu His Xaa Leu Tyr
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (10)..(10)
<223> OTHER INFORMATION: X is Diaminobutyric acid.

<400> SEQUENCE: 59

Asp Thr Arg Tyr Leu Glu Gln Leu His Xaa Leu Tyr
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: X is Diaminobutyric acid.

<400> SEQUENCE: 60

Leu Asp Thr Lys Tyr Leu Glu Gln Leu His Xaa Leu Tyr
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Asp modified with acetyl group

<400> SEQUENCE: 61

Xaa Thr Arg Tyr Leu Glu Gln Leu His Ala Leu Tyr
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Asp modified with acetyl group

<400> SEQUENCE: 62

Xaa Thr Arg Tyr Leu Glu Gln Leu His Glu Leu Tyr
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Ala modified with acetyl group

<400> SEQUENCE: 63

Xaa Thr Arg Tyr Leu Glu Gln Leu His Lys Leu Tyr
1               5                   10

<210> SEQ ID NO 64
```

```
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Asp modified with palmitoyl group
<220> FEATURE:
<221> NAME/KEY: MISC_FEATURE
<222> LOCATION: (14)..(14)
<223> OTHER INFORMATION: Epsilon-palmitoyl modified lysine

<400> SEQUENCE: 64

Xaa Thr Lys Tyr Leu Glu Gln Leu His Lys Leu Tyr Lys Xaa
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Synthetic

<400> SEQUENCE: 65

Leu Asp Thr Arg Tyr Leu Glu Gln Leu His Lys Leu Tyr
1               5                   10

<210> SEQ ID NO 66
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: All the amino acids are D-amino acids
<220> FEATURE:
<221> NAME/KEY: MISC_FEATURE
<222> LOCATION: (1)..(1)
<223> OTHER INFORMATION: Ile modified with palmitoyl group

<400> SEQUENCE: 66

Xaa Gln Arg Tyr Leu Lys His Leu Gln Glu Leu Tyr Arg Thr Asp
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: All the amino acids are D-amino acids
<220> FEATURE:
<221> NAME/KEY: MISC_FEATURE
<222> LOCATION: (1)..(1)
<223> OTHER INFORMATION: Ile modified with palmitoyl group

<400> SEQUENCE: 67

Xaa Gln Lys Tyr Leu Lys His Leu Gln Glu Leu Tyr Arg Thr Asp
1               5                   10                  15

<210> SEQ ID NO 68
<211> LENGTH: 14
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<223> OTHER INFORMATION: All the amino acids are D-amino acids
<220> FEATURE:
<221> NAME/KEY: MISC_FEATURE
<222> LOCATION: (1)..(1)
<223> OTHER INFORMATION: Gln modified with palmitoyl group

<400> SEQUENCE: 68

Xaa Arg Tyr Leu Lys His Leu Gln Glu Leu Tyr Arg Thr Asp
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: All the amino acids are D-amino acids
<220> FEATURE:
<221> NAME/KEY: MISC_FEATURE
<222> LOCATION: (1)..(1)
<223> OTHER INFORMATION: Arg modified with palmitoyl group

<400> SEQUENCE: 69

Xaa Tyr Leu Lys His Leu Gln Glu Leu Tyr Arg Thr Asp
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: All the amino acids are D-amino acids
<220> FEATURE:
<221> NAME/KEY: MISC_FEATURE
<222> LOCATION: (1)..(1)
<223> OTHER INFORMATION: Gln modified with palmitoyl group

<400> SEQUENCE: 70

Xaa Tyr Leu Lys His Leu Gln Glu Leu Tyr Arg Thr Asp
1               5                   10

<210> SEQ ID NO 71
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: All the amino acids are D-amino acids
<220> FEATURE:
<221> NAME/KEY: MISC_FEATURE
<222> LOCATION: (1)..(1)
<223> OTHER INFORMATION: Lys modified with palmitoyl group

<400> SEQUENCE: 71

Xaa Tyr Leu Lys His Leu Gln Glu Leu Tyr Arg Thr Asp
1               5                   10

<210> SEQ ID NO 72
<211> LENGTH: 15
<212> TYPE: PRT
<213> ORGANISM: Artificial Sequence
<220> FEATURE:
```

```
<223> OTHER INFORMATION: Synthetic
<220> FEATURE:
<221> NAME/KEY: MISC_FEATURE
<223> OTHER INFORMATION: All the amino acids are D-amino acids
<220> FEATURE:
<221> NAME/KEY: MISC_FEATURE
<222> LOCATION: (1)..(1)
<223> OTHER INFORMATION: Ile modified with palmitoyl group

<400> SEQUENCE: 72

Xaa Gln Arg Tyr Leu Lys His Leu Gln Gln Leu Tyr Arg Thr Asp
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: All the amino acids are D-amino acids
<220> FEATURE:
<221> NAME/KEY: MISC_FEATURE
<222> LOCATION: (1)..(1)
<223> OTHER INFORMATION: Ile modified with palmitoyl group

<400> SEQUENCE: 73

Xaa Gln Arg Tyr Leu Lys His Leu Gln Gln Leu Tyr Arg Thr Asn
1               5                   10                  15

<210> SEQ ID NO 74
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: All the amino acids are D-amino acids
<220> FEATURE:
<221> NAME/KEY: MISC_FEATURE
<222> LOCATION: (1)..(1)
<223> OTHER INFORMATION: Tyr modified with palmitoyl group

<400> SEQUENCE: 74

Xaa Leu Lys His Leu Gln Glu Leu Tyr Arg Thr Asp
1               5                   10

<210> SEQ ID NO 75
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: All the amino acids are D-amino acids
<220> FEATURE:
<221> NAME/KEY: MISC_FEATURE
<222> LOCATION: (1)..(1)
<223> OTHER INFORMATION: Gln modified with palmitoyl group

<400> SEQUENCE: 75

Xaa Arg Tyr Leu Lys His Leu Gln Glu Leu Tyr Arg Thr Asp Leu
1               5                   10                  15

<210> SEQ ID NO 76
<211> LENGTH: 12
<212> TYPE: PRT
<213> ORGANISM: Artificial Sequence
```

```
<220> FEATURE:
<223> OTHER INFORMATION: Synthetic
<220> FEATURE:
<221> NAME/KEY: MISC_FEATURE
<223> OTHER INFORMATION: All the amino acids are D-amino acids
<220> FEATURE:
<221> NAME/KEY: MISC_FEATURE
<222> LOCATION: (1)..(1)
<223> OTHER INFORMATION: Tyr modified with palmitoyl group

<400> SEQUENCE: 76

Xaa Leu Lys His Leu Gln Gln Leu Tyr Arg Thr Asn
1               5                  10

<210> SEQ ID NO 77
<211> LENGTH: 4
<212> TYPE: PRT
<213> ORGANISM: Artificial Sequence
<220> FEATURE:
<223> OTHER INFORMATION: Synthetic

<400> SEQUENCE: 77

Arg Gln Ile Lys
1

<210> SEQ ID NO 78
<211> LENGTH: 4
<212> TYPE: PRT
<213> ORGANISM: Artificial Sequence
<220> FEATURE:
<223> OTHER INFORMATION: Synthetic

<400> SEQUENCE: 78

Lys Gln Ile Lys
1

<210> SEQ ID NO 79
<211> LENGTH: 21
<212> TYPE: DNA
<213> ORGANISM: Artificial Sequence
<220> FEATURE:
<223> OTHER INFORMATION: Synthetic

<400> SEQUENCE: 79
gctcttactg actggcatga g                                           21

<210> SEQ ID NO 80
<211> LENGTH: 21
<212> TYPE: DNA
<213> ORGANISM: Artificial Sequence
<220> FEATURE:
<223> OTHER INFORMATION: Synthetic

<400> SEQUENCE: 80
caataccatt gacctgccga t                                           21

<210> SEQ ID NO 81
<211> LENGTH: 20
<212> TYPE: DNA
<213> ORGANISM: Artificial Sequence
<220> FEATURE:
<223> OTHER INFORMATION: Synthetic

<400> SEQUENCE: 81
aataccattg acctgccgat                                             20

<210> SEQ ID NO 82
```

```
<211> LENGTH: 18
<212> TYPE: DNA
<213> ORGANISM: Artificial Sequence
<220> FEATURE:
<223> OTHER INFORMATION: Synthetic

<400> SEQUENCE: 82
agcgactcaa actgccct                                                     18

<210> SEQ ID NO 83
<211> LENGTH: 21
<212> TYPE: DNA
<213> ORGANISM: Artificial Sequence
<220> FEATURE:
<223> OTHER INFORMATION: Synthetic

<400> SEQUENCE: 83
atgaacgcta cacactgcat c                                                 21

<210> SEQ ID NO 84
<211> LENGTH: 21
<212> TYPE: DNA
<213> ORGANISM: Artificial Sequence
<220> FEATURE:
<223> OTHER INFORMATION: Synthetic

<400> SEQUENCE: 84
ccatcctttt gccagttcct c                                                 21

<210> SEQ ID NO 85
<211> LENGTH: 23
<212> TYPE: DNA
<213> ORGANISM: Artificial Sequence
<220> FEATURE:
<223> OTHER INFORMATION: Synthetic

<400> SEQUENCE: 85
gttctcagcc caacaataca aga                                               23

<210> SEQ ID NO 86
<211> LENGTH: 19
<212> TYPE: DNA
<213> ORGANISM: Artificial Sequence
<220> FEATURE:
<223> OTHER INFORMATION: Synthetic

<400> SEQUENCE: 86
gtggacgggt cgatgtcac                                                    19

<210> SEQ ID NO 87
<211> LENGTH: 20
<212> TYPE: DNA
<213> ORGANISM: Artificial Sequence
<220> FEATURE:
<223> OTHER INFORMATION: Synthetic

<400> SEQUENCE: 87
cagaagaatg gaagagtcag                                                   20

<210> SEQ ID NO 88
<211> LENGTH: 20
<212> TYPE: DNA
<213> ORGANISM: Artificial Sequence
<220> FEATURE:
<223> OTHER INFORMATION: Synthetic

<400> SEQUENCE: 88
```

```
cagatatgca gggagtcacc                                          20

<210> SEQ ID NO 89
<211> LENGTH: 20
<212> TYPE: DNA
<213> ORGANISM: Artificial Sequence
<220> FEATURE:
<223> OTHER INFORMATION: Synthetic

<400> SEQUENCE: 89 gtaaccgtt gaaccccatt                                           20

<210> SEQ ID NO 90
<211> LENGTH: 20
<212> TYPE: DNA
<213> ORGANISM: Artificial Sequence
<220> FEATURE:
<223> OTHER INFORMATION: Synthetic

<400> SEQUENCE: 90
ccatccaatc ggtagtagcg                                          20
```